(12) United States Patent
Merten et al.

(10) Patent No.: US 10,710,078 B2
(45) Date of Patent: Jul. 14, 2020

(54) MICROFLUIDIC DROPLET DETECTION AND SORTING

(71) Applicant: EUROPEAN MOLECULAR BIOLOGY LABORATORY, Heidelberg (DE)

(72) Inventors: Christoph A. Merten, Heidelberg (DE); Hongxing Hu, Heidelberg (DE); David Eustace, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 0 days.

(21) Appl. No.: 15/569,201

(22) PCT Filed: Apr. 29, 2016

(86) PCT No.: PCT/EP2016/059658
§ 371 (c)(1),
(2) Date: Oct. 25, 2017

(87) PCT Pub. No.: WO2016/174229
PCT Pub. Date: Nov. 3, 2016

(65) Prior Publication Data
US 2018/0104693 A1    Apr. 19, 2018

(30) Foreign Application Priority Data

Apr. 30, 2015   (EP) ..................... 15165915

(51) Int. Cl.
*B01L 3/00*   (2006.01)
*G01N 15/14*   (2006.01)
(Continued)

(52) U.S. Cl.
CPC .... *B01L 3/502784* (2013.01); *G01N 15/1484* (2013.01); *G01N 33/5094* (2013.01);
(Continued)

(58) Field of Classification Search
CPC ............ B01L 3/502784; B01L 3/5027; B01L 3/502769; B01L 3/502; B01L 3/50;
(Continued)

(56) References Cited

U.S. PATENT DOCUMENTS

2003/0178310 A1   9/2003   Gawad et al.
2006/0194307 A1   8/2006   Yasuda et al.
(Continued)

FOREIGN PATENT DOCUMENTS

CN    102539733 A    7/2012
JP    2003-287519 A    10/2003
(Continued)

OTHER PUBLICATIONS

Guo et al, Droplet nnicrofluidics for high-throughput biological assays, Lab Chi, 2012, 12, 2146-2155. (Year: 2012).*
(Continued)

*Primary Examiner* — Christine T Mui
(74) *Attorney, Agent, or Firm* — Hamre, Schumann, Mueller & Larson, P.C.

(57) ABSTRACT

The present invention relates to the field of microfluidics and in particular to methods for detecting microfluidic droplets and particles within droplets, as well as sorting the droplets. These methods allow for quantifying properties and activities of the particles within the droplets. For this purpose, the invention provides microfluidic droplets comprising suitably labelled particles. The invention also provides microfluidic devices and systems having properties which make them particularly suitable for use in the methods of the invention.

11 Claims, 8 Drawing Sheets

(51) Int. Cl.
  G01N 33/50 (2006.01)
  G01N 33/58 (2006.01)
  G01N 33/48 (2006.01)

(52) U.S. Cl.
  CPC ........ *G01N 33/58* (2013.01); *B01L 3/502761* (2013.01); *B01L 2200/0652* (2013.01); *G01N 15/1459* (2013.01); *G01N 2015/149* (2013.01)

(58) Field of Classification Search
  CPC ..... B01L 2200/0652; B01L 2200/0647; B01L 2200/06; G01N 15/1484; G01N 15/14; G01N 14/10; G01N 14/00; G01N 33/5094; G01N 33/5005; G01N 33/50; G01N 33/48; G01N 33/58
  USPC .......................................... 422/502, 500, 50
  See application file for complete search history.

(56) References Cited

U.S. PATENT DOCUMENTS

| | | | |
|---|---|---|---|
| 2007/0243627 A1* | 10/2007 | Takayama | B01L 3/502715 436/180 |
| 2010/0075436 A1 | 3/2010 | Urdea et al. | |
| 2010/0092955 A1* | 4/2010 | Harriman | G01N 33/5436 435/6.19 |
| 2011/0275063 A1 | 11/2011 | Weitz et al. | |
| 2014/0008307 A1 | 1/2014 | Guldiken et al. | |

FOREIGN PATENT DOCUMENTS

| | | |
|---|---|---|
| JP | 2006-180810 A | 7/2006 |
| JP | 2011-512842 A | 4/2011 |
| WO | 2009/111014 A2 | 9/2009 |
| WO | 2011/042564 | 4/2011 |
| WO | 2013134261 A1 | 9/2013 |
| WO | 2015048173 A2 | 4/2015 |

OTHER PUBLICATIONS

Li et al., "A review of microfabrication techniques and dielectrophoretic microdevices for particle manipulation and separation," Journal of Physics D: Applied Physics (American Institute of Physics), vol. 47, No. 6, Jan. 1, 2014, pp. 1-29.
Lagus, T et al., "Throughput Single-cell and Multiple-cell Micro-encapsulation," Journal of Visualized Experiments, No. 64, Jun. 15, 2012, pp. 1-7.
Lagus, T et al., "A review of the theory, methods and recent applications of high-throughput single-cell droplet microfluidics," Journal of Physics D: Applied Physics, Institute of Physics Publishing, Ltd., GB, vol. 46, No. 11, Feb. 22, 2013.
Hu et al., "Efficient cell pairing in droplets using dual-color sorting," Lab on a Chip (Royal Society for Chemistry), vol. 15, No. 20, Aug. 17, 2015.
International Search Report and Written Opinion, for corresponding PCT/EP2016/059658 application, dated Jun. 23, 2016 (14 pages).
International Preliminary Report on Patentability for corresponding International Application No. PCT/EP2016/059658, dated Nov. 9, 2017 (11 pages).
Office Action, Chinese Patent Application No. 201680036954.5, dated Apr. 8, 2019, with English translation (25 pages).
English summary of Japanese Office Action dated Apr. 28, 2020 (1 page).

* cited by examiner

Figure 7:
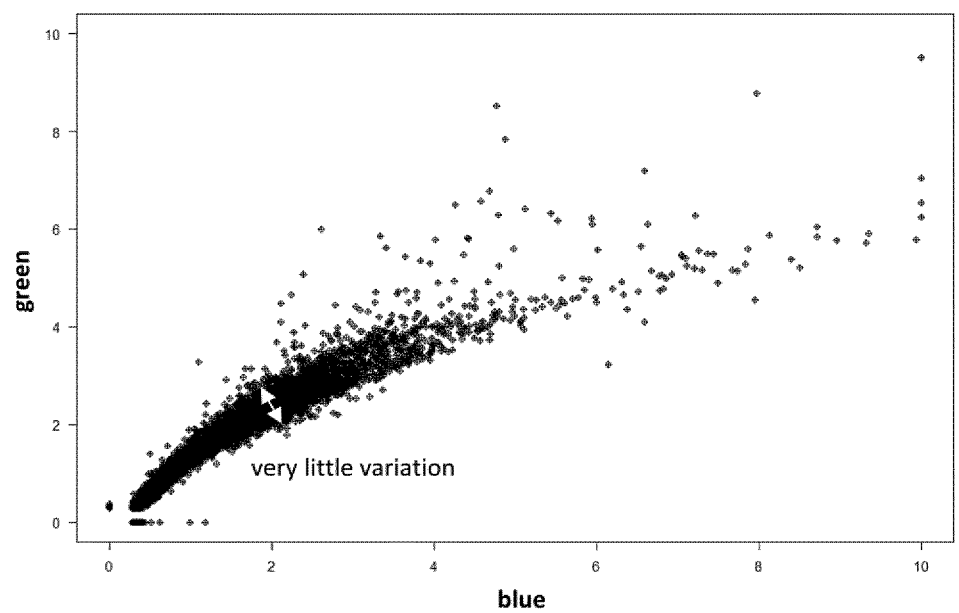

Figure 7 A/B
A
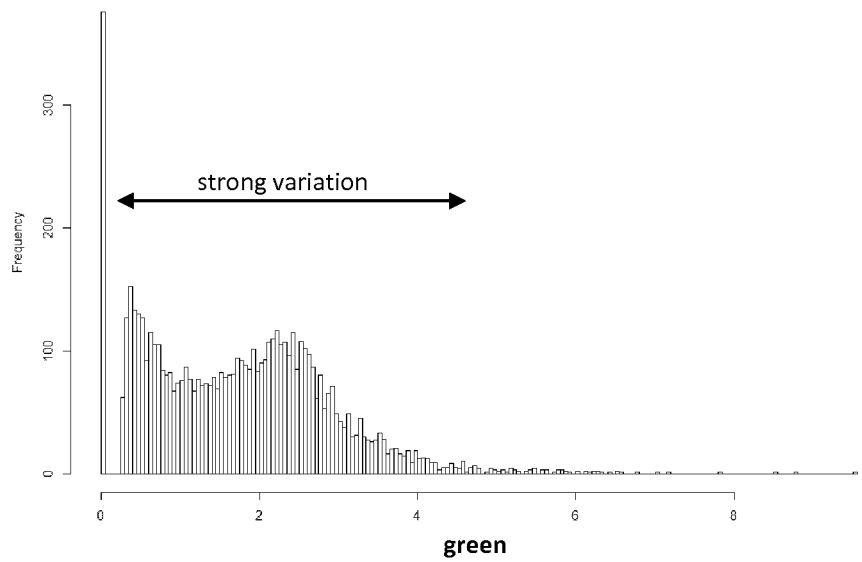
B
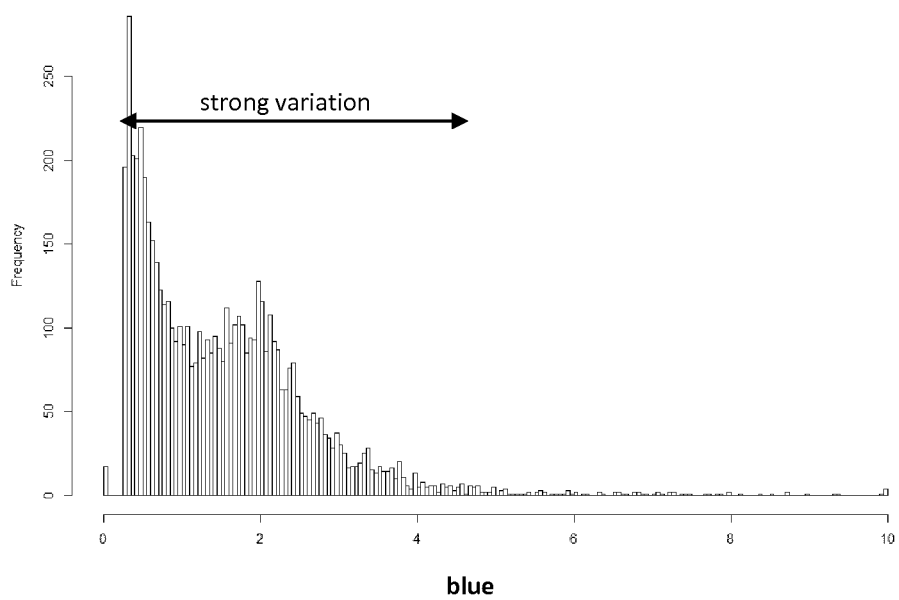

MICROFLUIDIC DROPLET DETECTION AND SORTING

CROSS REFERENCE TO RELATED APPLICATIONS

This application is the U.S. national phase application, pursuant to 35 U.S.C. § 371, of PCT International Application No. PCT/EP2016/059658, filed Apr. 29, 2016, designating the United States and published in English, which claims priority to and the benefit of European Patent Application No. 15165915.8, filed Apr. 30, 2015, which is incorporated herein by reference in its entirety.

FIELD OF THE INVENTION

The present invention relates to the field of microfluidics and in particular to methods for detecting microfluidic droplets and particles within droplets, as well as sorting the droplets. These methods allow for quantifying properties and activities of the particles within the droplets. For this purpose, the invention provides microfluidic droplets comprising suitably labelled particles. The invention also provides microfluidic devices and systems having properties which make them particularly suitable for use in the methods of the invention.

BACKGROUND OF THE INVENTION

Droplet based microfluidics holds great potential for high throughput screening applications. The encapsulation of single cells into droplets allows screening of cell products such as antibodies at very high throughput, e.g. up to several hundred thousand samples per day. For example, individual antibody-secreting cells (e.g. hybridoma- or B-cells) can be encapsulated into droplets together with a recombinant drug target of interest, such as an enzyme. Addition of a fluorogenic substrate of the enzyme will then reveal which droplets contain a cell releasing antibodies which inhibit enzymatic activity and facilitate the specific sorting of these. However, for many screening applications, it would be very useful to co-encapsulate (in addition to the antibody secreting cell) another reporter cell, rather than a recombinant enzyme. This reporter cell could mediate a fluorescence signal (e.g. expression of a reporter enzyme which can easily be detected in droplets; such as (3-Gal) upon the desired effect of an antibody, such as the stimulation or inhibition of cellular pathways upon antibody binding of G protein-coupled receptors (GPCRs). GPCRs are the targets of most best-selling drugs and about 40% of all prescription pharmaceuticals.

A crucial step for this kind of screens is the generation of droplets hosting both cell types, optionally at the single cell level. Non-deterministic cell encapsulation is limited by Poisson statistics, meaning that the number of cells per droplets varies significantly. Alternative deterministic encapsulation procedures have been described, however, until today the reliable co-encapsulation of two different cell types has not been demonstrated, especially not at single-cell level. Therefore, cell-based assays requiring the co-encapsulation of two different cell types at the single cell level (as required for drug screening; e.g. one B-cell secreting antibodies and another reporter cell indicating the effect of the antibody on a cellular target) can hardly be performed in droplets. This is due to the fact that the cell occupancy in each droplet cannot be controlled tightly, including controlled co-encapsulation of cells and beads as required for antibody binding assays. Furthermore, the quantitative analysis of antibody binding is challenging, as the bead (and any fluorescently labelled objects bound to it) can float out of the focal plane and/or out of the centre of the laser spot (having the highest intensity).

To overcome these limitations, the inventors have developed novel sorting devices and sorting methods allowing for the selection of droplets for any desired droplet occupancy, including the presence of two different cell types such as an antibody secreting cell (or any other "effector cell") and a reporter cell. Furthermore, they have developed a system, more specifically a particular labelling approach of binding partners in droplets, which allows for quantitative binding assays, even if the object of interest is out of the focal plane or outside the most intense laser spot. Taken together, this should have manifold applications in drug screening and antibody discovery, a market with annual sales exceeding 50 billion USD.

SUMMARY OF THE INVENTION

In a first aspect, the present invention relates to a microfluidic droplet comprising a single first particle associated with an amount of a first detectable label, and a potential particle binding partner associated with an amount of a second detectable label, wherein the amount of the first detectable label is known and/or substantially identical to the amount of the first detectable label associated with a single further particle comprised in a further microfluidic droplet.

In a second aspect, the present invention relates to a method for quantifying the binding between a particle and a potential particle binding partner in a microfluidic droplet according to the first aspect, comprising the steps of
(i) measuring the signal of the first detectable label,
(ii) measuring the signal of the second detectable label, and
(iii) normalizing the signal of the second detectable label using the signal of the first detectable label,
wherein the normalized signal of the second detectable label represents the quantity of binding between the particle and the potential particle binding partner.

In a third aspect, the present invention relates to a method for detecting one or more particles comprised in a microfluidic droplet, comprising the steps of:
(a) feeding a microfluidic droplet comprising one or more particles into a detection channel comprising a detection point,
(b) constricting at least the vertical movement of the particle(s) within the microfluidic droplet at least at the detection point in the detection channel, compared to the same microfluidic droplet when having a spherical shape, and
(c) detecting at least one particle comprised in the microfluidic droplet at the detection point.

In a fourth aspect, the present invention relates to a population of microfluidic droplets, wherein more than 50% of the microfluidic droplets comprise each a single particle of at least two types, especially a single cell of at least two cell types (i.e. two single cells each of a different cell type).

In a fifth aspect, the present invention relates to a microfluidic device for detecting one or more particles comprised in a microfluidic droplet, comprising a detection channel with a detection point, characterized in that the device is designed such that at least the vertical movement of the particle(s) within the microfluidic droplet is or can be constricted in the detection channel at least at the detection point, compared to the same microfluidic droplet when having a spherical shape.

In a sixth aspect, the present invention relates to a microfluidic device for detecting one or more particles comprised in a microfluidic droplet, comprising a detection channel with a detection point, characterized in that it comprises, downstream of the detection channel, a sorting channel with a sorting junction for separating microfluidic droplets based on the signal of the detected particle(s), wherein the distance between the sorting junction and the detection point is 500 µm or less, and preferably less than 10× the diameter of the microfluidic droplet in spherical form.

In a seventh aspect, the present invention relates to a microfluidic device for detecting one or more particles comprised in a microfluidic droplet, comprising a detection channel with a detection point, characterized in that it comprises, downstream of the detection channel, a sorting channel with a sorting junction for separating microfluidic droplets based on the signal of the detected particle(s), wherein the sorting and/or detection channel of the device is kinked or has a bend downstream of the detection point and upstream of the sorting junction.

In an eighth aspect, the present invention relates to a microfluidic device for detecting one or more particles comprised in a microfluidic droplet, comprising a detection channel with a detection point, characterized in that it comprises, downstream of the detection channel, a sorting channel with a sorting junction for separating microfluidic droplets based on the signal of the detected particle(s), wherein the device further comprises one or more fluid inlets upstream of the sorting junction and downstream of the detection point for injecting fluid into the sorting channel.

In a ninth aspect, the present invention relates to a microfluidics system, comprising:

a microfluidic device according to the fifth, sixth, seventh and/or eighth aspect, and a detection means for detecting at least one particle comprised in a microfluidic droplet in the detection channel at the detection point.

In a tenth aspect, the present invention relates to the use of microfluidic droplets, devices and systems of the invention for the methods of invention.

LEGENDS TO THE FIGURES

Figure 1:
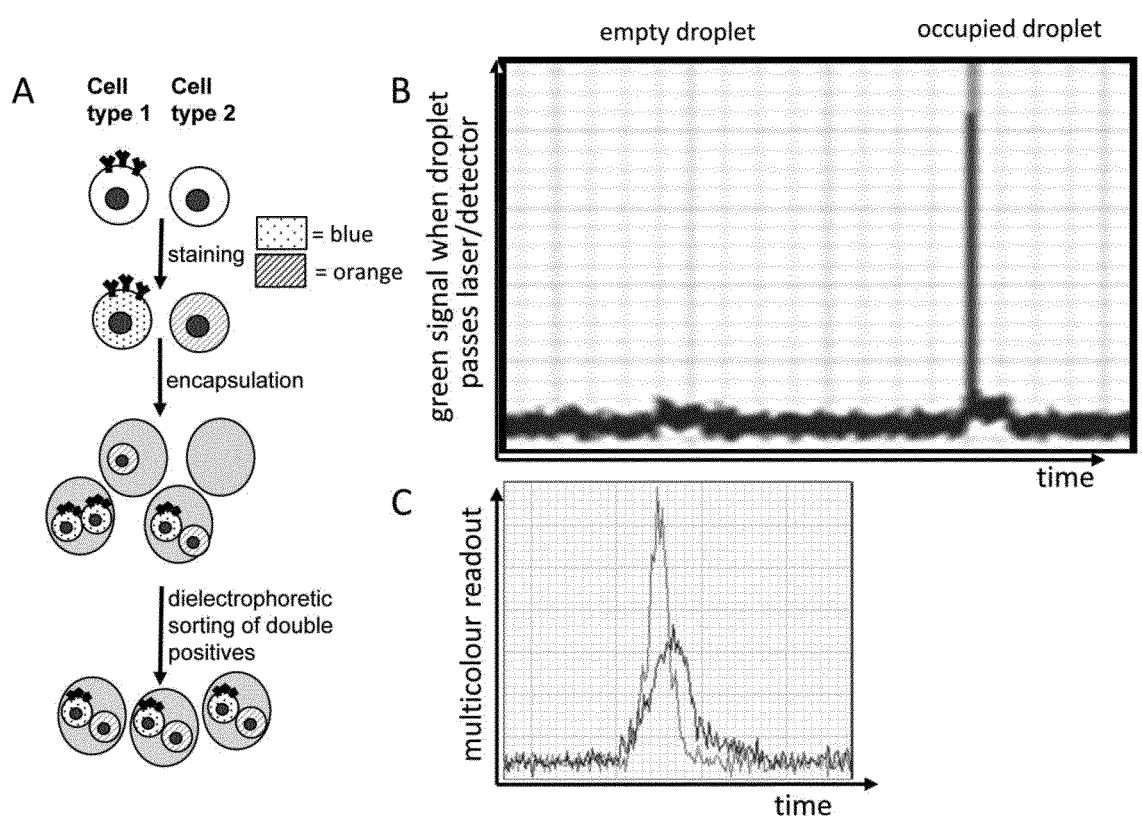

FIG. 1: Co-encapsulation of two different cell types. A) Active sorting of droplets hosting exactly one cell of each type can be achieved by staining with fluorescent dyes. Prior to encapsulation, each cell type is stained with a different fluorescence dye (e.g. Calcein-AM-blue and Calcein red-orange). Subsequent to the formation of droplets, dielectrophoretic sorting for samples showing double positive fluorescence signals is carried out. Only these droplets are applied to the downstream screening procedure (using an assay signal in the green channel), as initiated by off-chip incubation and subsequent re-injection into the second microfluidic device. B) Fluorescence signals of empty (left) and occupied (right) droplets using single (green) colour staining. C) Fluorescence signal of a double-positive sample showing a fluorescence signal in both channels (upper and lower peak).

Figure 2:
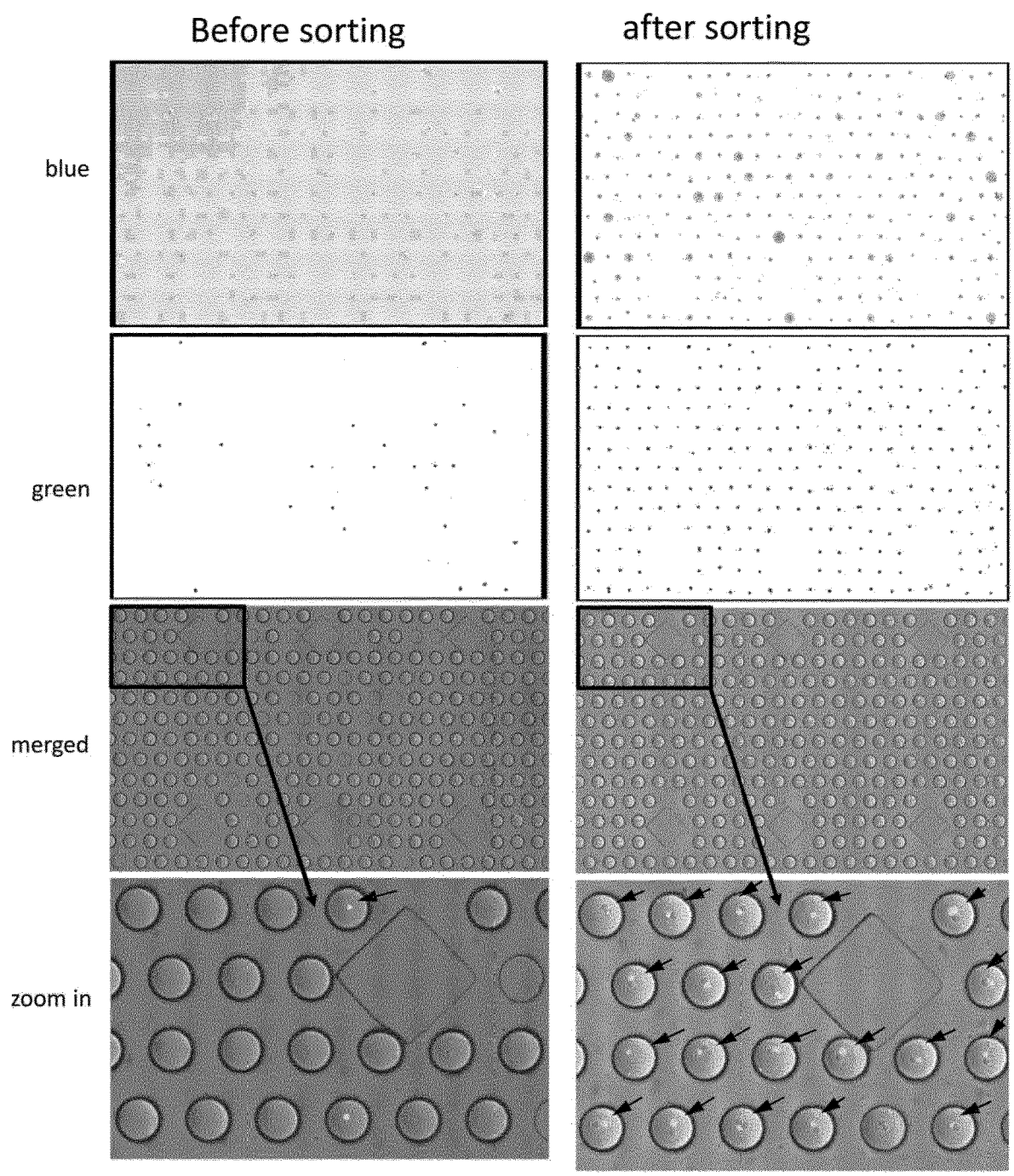

FIG. 2: Enrichment of droplets hosting two different cell types by sorting. Hybridoma cells were stained with either calcein-AM (visible in the green channel) or calcein-violet (visible in the blue channel). Subsequently, droplets showing one peak in each fluorescence channel were sorted and trapped in a second microfluidic chip. A clear enrichment of droplets hosting cells of both types (indicated by arrows) after sorting can be observed.

Figure 3:
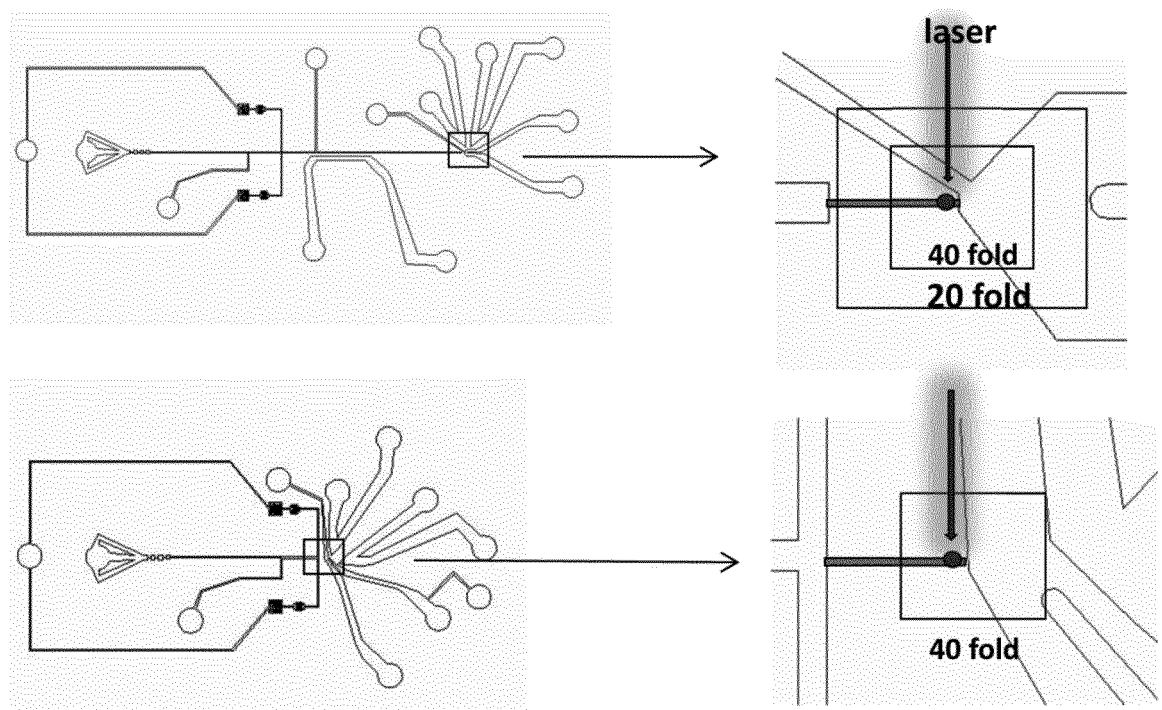

FIG. 3: Design of the new sorting chip. To increase the sensitivity when measuring the fluorescence of particles/cells encapsulated into droplets, several features have been added as compared to conventional sorting devices. While for previously described droplet sorters large enough to handle 100 µm droplets (as required for the cultivation of eukaryotic cells) the detection point and the sorting divider do not fit into the same field of view when using a 40× objective (inner rectangle on top). However, this is the case for the newly developed sorting chip (bottom). To enable a very compact design, the sorting electrodes and the sorting channels have been tilted 45° relative to the detection channel. Furthermore, the detection channel is narrower and shallower as compared to the remaining channels of the design (bottom right). This way, droplets are compressed in the y- and z-axis thus restricting the spatial freedom of encapsulated particles/cells. Furthermore an additional oil inlet in between the detection point and the sorting divider allows to fine tune the trajectory of the droplets at the sorting junction.

Figure 4:
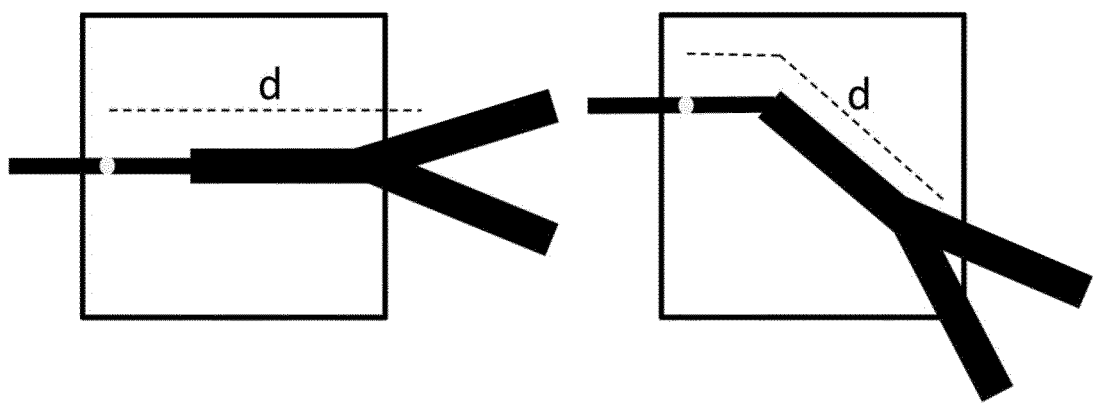

FIG. 4: Advantage of having the detection channel and sorting channel in a 45° angle. In a normal sorting configuration (left), the distance (d) between the detection point (white) and the sorting junction does not fit into the same field of view (rectangle) when using high magnifications as required for sensitive measurements. This makes it very difficult to adjust all sorting parameters (e.g. flow rates, duration of electric, acoustic or optic pulses or valve-opening times) for reliable sorting. In contrast, if the sorting channel is arranged in an angle relative to the detection point (right), all relevant features fit into the same field of view. Note that the distance d (illustrated as a black line) is the same in both cases.

Figure 5:
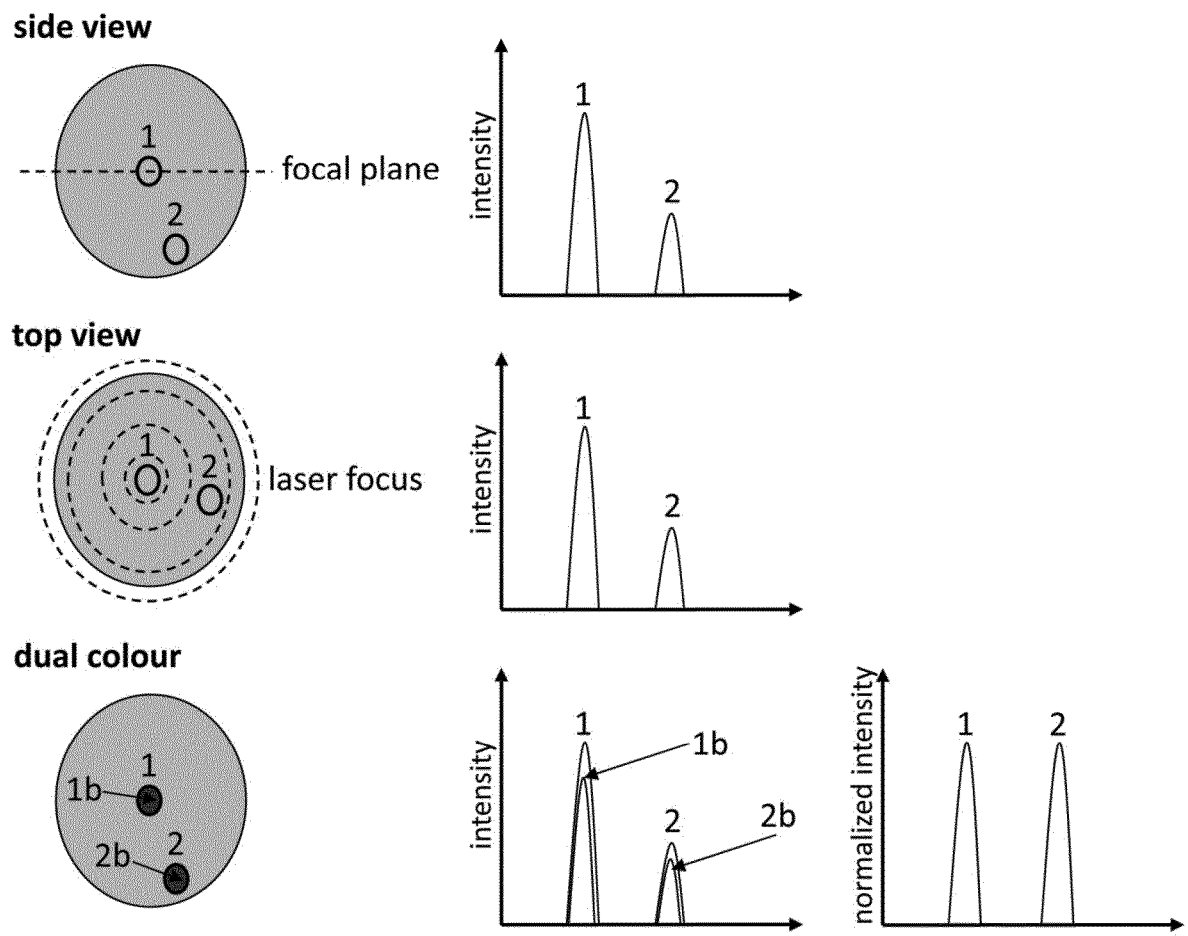

FIG. 5: Influence of the position of a fluorescence particle in a droplet on the measured fluorescence intensity. Even when using fluorescent particles with the same number of fluorophores (e.g. bound green fluorescently-labelled antibodies), the measured fluorescence signal can vary. For example, if the particle is outside the focal plane (top left, 2), the fluorescence peak (top right) is weaker as compared to a particle within the focal plane (1). The same is also true for particles outside the centre of the laser focus (middle panel). However, this problem can be overcome, by using a second fluorescent colour (e.g. an orange fluorescence dye; indicated by arrows and/or the label "b" in the bottom panel) on the beads: While the individual colours still vary depending on the position of the bead within the droplet, the normalized signal (e.g. green/orange) does not, or at least to a much lower extent. This way, the number of bound green antibodies can be measured quantitatively, independently of the position of the bead inside the droplet.

Figure 6:
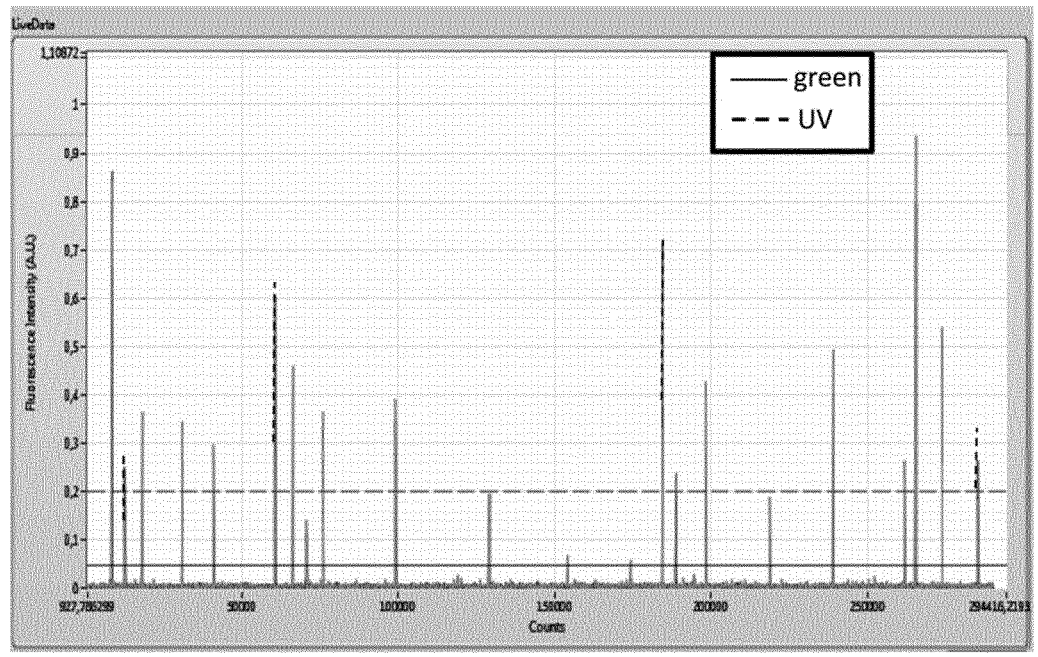
Figure 6:
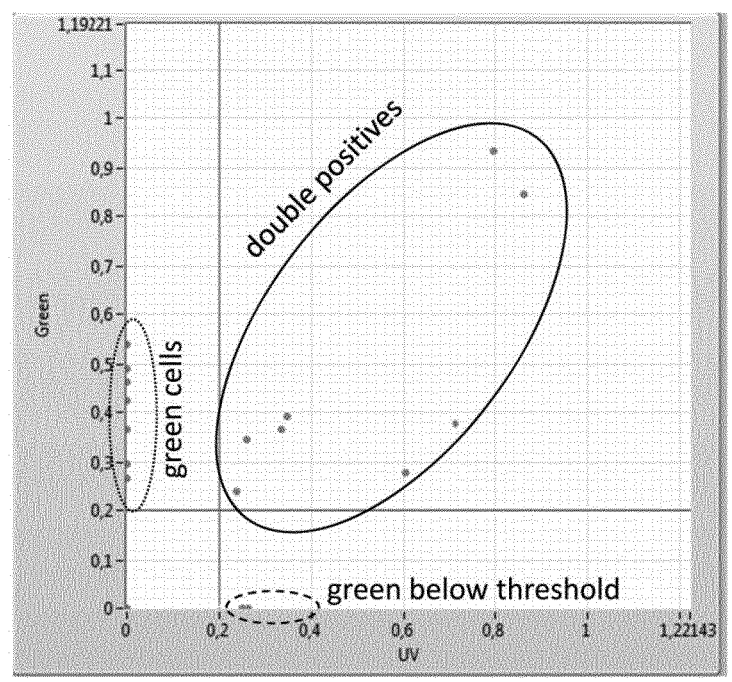

FIG. 6: Normalization of fluorescence signals. To demonstrate the feasibility of the approach, cells have been stained with either Calcein green, only, or additionally also with Calcein-blue. When plotting the signals of the individual fluorescence channels (top) against each other (bottom) different populations become visible: Cells that are only stained with the green dye show strongly varying intensities, caused by their arbitrary position within the droplet (right, dotted ellipse). However, all double stained cells are lying on a straight line (right, solid ellipse) meaning that their normalized signal is almost identical.

FIG. 7: Normalization of Fluoresbrite bead signals. AB) 6 µm Fluoresbrite beads in droplets show a very wide distribution of fluorescence intensities when only a single fluorescence channel (e.g. green (A) or blue range (B)) is analyzed (indicated by black arrows), due to the beads freely floating inside the droplets. C) When normalizing the green signal to the blue signal, the effect of the beads floating inside the droplets can be minimized (indicated by the white arrow).

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland) and in "Encyclopedia of Microfluidics and Nanofluidics", Springer Reference, Volume 1.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In a first aspect, the present invention relates to a microfluidic droplet comprising a single first particle associated with an amount of a first detectable label, and a potential particle binding partner associated with an amount of a second detectable label, wherein the amount of the first detectable label is known and/or substantially identical to the amount of the first detectable label associated with a single further particle comprised in a further microfluidic droplet.

Preferably, also the amount of the second detectable label is known and/or substantially identical for all potential particle binding partners.

The term "microfluidic droplet" refers to an aqueous microcompartment of a certain size that encapsulates an aqueous liquid. The size of the microfluidic droplet is usually expressed as the diameter of the droplet when in a spherical shape. The diameter is generally between 20 and 400 µm, and preferably between 30 and 350 µm, between 40 and 300 µm, between 40 and 250 µm, between 40 and 200 µm or between 40 and 100 µm (wherein each narrower range is preferred to the foregoing broader ranges and "between" includes the values mentioned). In a preferred embodiment, the diameter of the microfluidic droplet is between 2 and 20 times the diameter of the largest particle (e.g. the first particle or a further particle) in the droplet, preferably between 3 and 18 times, between 4 and 16 times, or between 5 and 14 times or between 6 and 12 times (wherein each narrower range is preferred to the foregoing broader ranges and "between" includes the values mentioned). Preferably, the diameter of the droplet is defined by both the above absolute and relative parameters. For example, the diameter is (i) between 20 and 400 µm, between 30 and 350 µm, between 40 and 300 µm, between 40 and 300 µm, between 40 and 250 µm, between 40 and 200 µm or between 40 and 100 µm and between 2 and 20 times the diameter of the largest particle (e.g. the first particle or a further particle) in the droplet, (ii) between 20 and 400 µm, between 30 and 350 µm, between 40 and 300 µm, between 40 and 300 µm, between 40 and 250 µm, between 40 and 200 µm or between 40 and 100 µm and between 4 and 16 times the diameter of the largest particle (e.g. the first particle or a further particle) in the droplet, or (iii) between 20 and 400 µm, between 30 and 350 µm, between 40 and 300 µm, between 40 and 300 µm, between 40 and 250 µm, between 40 and 200 µm or between 40 and 100 µm and between 6 and 12 times the diameter of the largest particle (e.g. the first particle or a further particle) in the droplet.

Alternatively, the size of the microfluidic droplet can also be defined by volume. For example, it is usually less than 1 microlitre (µl). Preferably, it is less than 500 nanolitres (nl), less than 250, less than 150, less than 100 or less than 50 nl. In a preferred embodiment, it is between 0.05 and 150 nl, preferably between 0.05 and 125 nl, between 0.05 and 100 nl, between 0.05 and 80 nl, or between 0.05 and 4 nl (wherein each narrower range is preferred to the foregoing broader ranges and "between" includes the values mentioned).

A wide variety of compartmentalisation or microencapsulation procedures are available (Benita, S., Ed. (1996). Microencapsulation: methods and industrial applications. Drugs and pharmaceutical sciences. Edited by Swarbrick, J. New York: Marcel Dekker) and may be used to create the microfluidic droplet used in accordance with the present invention. Indeed, more than 200 microencapsulation or compartmentalisation methods have been identified in the literature (Finch, C. A. (1993) Encapsulation and controlled release. *Spec. Publ.-R. Soc. Chem.* 138, 35). These include membrane enveloped aqueous vesicles such as lipid vesicles (liposomes) (New, R. R. C., Ed. (1990). Liposomes: a practical approach. The practical approach series. Edited by Rickwood, D. & Hames, B. D. Oxford: Oxford University Press) and non-ionic surfactant vesicles (van Hal, D. A., Bouwstra, J. A. & Junginger, H. E. (1996). Nonionic surfactant vesicles containing estradiol for topical application. In *Microencapsulation: methods and industrial applications* (Benita, S., ed.), pp. 329-347. Marcel Dekker, New York.). Preferably, the microcompartments of the present invention are formed from emulsions; heterogeneous systems of two immiscible liquid phases with one of the phases dispersed in the other as droplets of microscopic size (Becher, P. (1957) Emulsions: theory and practice. Reinhold, N.Y.; Sherman, P. (1968) Emulsion science. Academic Press, London; Lissant, K. J., ed Emulsions and emulsion technology. Surfactant Science New York: Marcel Dekker, 1974; Lissant, K. J., ed. Emulsions and emulsion technology. Surfactant Science New York: Marcel Dekker, 1984). Emulsions may be produced from any suitable combination of immiscible liquids. Preferably the emulsion of the present invention has water (containing a particle and other components) as the phase present in the form of droplets and a hydrophobic, immiscible liquid (preferably an oil) as the surrounding matrix in which these droplets are suspended. Such emulsions are termed 'water-in-oil'. This has the advantage that the aqueous phase is compartmentalised in discrete droplets. The external phase, preferably being a hydrophobic oil, generally is inert. The emulsion may be stabilized by addition of one or more surface-active agents (surfactants). These surfactants act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash, M. and Ash, I. (1993) Handbook of industrial surfactants. Gower, Aldershot). Suitable oils are listed below.

Preferably, the aqueous microcompartments are created, handled and/or controlled in a microfluidic system. This technology is based on the manipulation of continuous liquid flow through microfabricated channels. Actuation of liquid flow is implemented either by external pressure sources, external mechanical pumps, integrated mechanical micropumps, or by combinations of capillary forces and electrokinetic mechanisms. Process monitoring capabilities in continuous-flow systems can be achieved with highly sensitive microfluidic flow sensors based on MEMS technology which offer resolutions down to the nanoliter range.

Microfluidic devices typically consist of networks of channels of approximately ten to a few hundred micrometers in diameter into which small quantities of reagents can be injected in a specific sequence, mixed and incubated for a specified time. Assays can be highly parallelized by generating independent compartments using valves (pinching off specific regions of the channels) or two-phase microfluidics, in which aqueous droplets surrounded by an immiscible oil phase serve as closed vessels. These approaches enable drastically reduced assay volumes (pico-nanoliters) and strongly improved throughput. For example, droplets can be generated at rates of more than 1,000 per second. Furthermore, microfluidic modules for the splitting, fusion and sorting of droplets at similar rates have been developed, thus providing a repertoire of manipulations mimicking classical bench top procedures.

In a preferred embodiment (applying to all aspects herein), the device, in particular the channels, is/are large enough to handle droplets comprising eukaryotic cells. In other words, the device, in particular the channels, is/are large enough to handle droplets of the sizes described herein, in particular 100 µm droplets.

Thus, the microcompartment described herein is also termed "microfluidic droplet", e.g. of a water-in-oil emulsion (Schaerli and Hollfelder, The potential of microfluidic water-in-oil droplets in experimental biology. Mol Biosyst (2009) vol. 5 (12) pp. 1392-404).

The "immiscible liquid" is preferably a hydrophobic liquid, preferably an oil. The oil phase should allow the microcompartments to be stable against coalescence, have a viscosity that is close to that of water, and/or be inert with respect to the biological reagents contained in them. Several oils can be used. Low-viscosity silicone oils swell. Polydimethylsiloxane, also called PDMS or dimethicone. PDMS is a polymer widely used for the manufacture of microfluidic chips, and it is a mineral-organic polymer (a structure containing carbon and silicon of the siloxane family), which can change the cross-sectional dimensions of microfluidic channels and influencing the flow properties of microfluidic devices if swelling occurs. Silicone oils can also be used in microfluidic devices fabricated in glass, which are impermeable to these oils. High-viscosity silicone oils can be used in PDMS devices with minimal swelling at the expense of significantly increasing the pressures required to pump them through the microchannels. Hydrocarbon oils can also be obtained in a range of viscosities and have the benefit that there are a large number of commercially available surfactants for them that can stabilize aqueous-in-oil emulsions. However, they also swell PDMS and tend to exhibit poor retention of encapsulated organic reagents, which are often partially soluble in these oils. The preferred oils for use in the methods of the invention are fluorocarbon oils (or flourinated oils), because even low-viscosity versions of these oils do not swell PDMS. In addition, they tend to exhibit excellent retention of reagents in the drops and have high solubility for gases, allowing oxygen and carbon dioxide to passively diffuse in and out of the microcompartments, for unperturbed cellular respiration. This allows cells to survive in fluorocarbon oil emulsions for hours after encapsulation. A disadvantage of fluorocarbon oils, however, is that, due to their much lower prevalence compared with silicone and hydrocarbon oils, there are fewer commercially available surfactants for stabilizing aqueous-in-fluorocarbon emulsions. Surfactants are useful for reducing the surface tension of the oil-water interface and minimizing droplet coalescence. The choice of which surfactant to use is also important for limiting the transfer of reagents between microcompartments. A comprehensive review of surfactants for droplet-based microfluidics is given in Baret (2012 *Lab Chip* 12, 422). The surfactants utilized in droplet-based microfluidics normally consist of a hydrophilic head group and hydrophobic tail. The amphiphilic character of these molecules allows them to assemble at the oil-water interface of the droplet, thereby lowering its interfacial tension and enhancing stability. The chemical properties of the head group of the surfactant impact the biocompatibility of the droplet interface. Surfactants with non-ionic head groups are preferred, as they minimize the adsorption of macromolecules such as proteins and DNA to the droplet interface, minimally impacting the methods of the invention. Suitable fluorosurfactants that can be readily synthesized in the lab are known in the art and described, e.g., in Clausell-Tormos J et al 2008 *Chem. Biol.* 15, 427-37 or Sadtler et al. 1996 *Angew. Chem. Int. Edn Engl.* 35, 1976-8. Additives to the aqueous phase can also enhance biocompatibility by increasing the retention of small molecules in the droplets and minimizing adsorption at the oil-water interface. Different oils can be mixed to optimize the properties of the emulsion for a particular application and methods for easily characterizing the properties of the combination that has been selected are known in the art (Kaltenbach et al. 2012 *Lab Chip* 12, 4185).

The term "particle" refers to any object small enough to fit into the microfluidic droplet and which can be labeled with a detectable label defined herein. Preferably, it is selected from the group consisting of a cell, a bead, a virus, a protein and a nanoparticle. The cell can be any prokaryotic or eukaryotic cell. Preferably, it is a eukaryotic cell, e.g. a yeast cell, plant cell or animal cell. Animal cells include insect, nematode, fish and mammalian cells. More preferably it is mammalian cell, e.g. a mouse, rat, monkey or human cell. For example, it can be a random cell of a heterogeneous cell population (e.g. from a tissue) or it can be a specifically selected cell, selected, e.g., by FACS. Also, it can be a cell from cell line or a homogeneous culture, for example of a primary cell, wherein "primary" means derived directly from a tissue or organism and not manipulated to have altered properties, e.g. to divide indefinitely. Other examples for cells are developing cells, stem cells or cancer cells. Preferred examples of cells are antibody-producing cells (e.g. B cells or hybridoma cells) and reporter cells for example signaling, preferably by fluorescence, the effect of the antibody produced by the antibody-producing cell on the reporter cell (e.g. the activation or inhibition of a receptor, preferably a G-protein coupled receptor).

The "bead" (also termed "microbead") is a uniform polymer particle with a diameter of up to 1 micrometre, preferably of 0.5 to 500 µm, and with a surface to which biological entities such as cells, proteins including antibodies and/or nucleic acids as well as detectably labels as described below can bind or be coupled. The beads referred to herein are usually polyethylene or polystyrene beads or beads made of gel matrices, for example coated with protein/peptide/antigen, e.g. cellular antigen (e.g. a cell surface antigen).

The term "virus" refers to a small infectious agent replicating only inside living cells of a host organism. Preferably, it is a pathogenic virus, more preferably a virus pathogenic in mammals, in particular humans, e.g. from the class of herpesviridae, adenoviridae, papillomaviridae, polyomaviridae, poxviridae, anelloviridae, parvoviridae, reoviridae, coronaviridae, astroviridae, caliciviridae, flaviviridae, picornaviridae, togaviridae, rhabdoviridae, filoviridae, paramyxoviridae, arenaviridae, bunyaviridae, orthomyxoviridae, retroviridae or hapadnaviridae.

The term "protein" as used herein indicates a polypeptide with a particular secondary and tertiary structure that can interact with another analyte and in particular, with other biomolecules including other proteins, DNA, RNA, lipids, metabolites, hormones, chemokines, and small molecules. In can be a natural (i.e. unaltered by man) or a recombinant protein. Preferably, other than proteins defined above such as antibodies, it is a cell surface-displayed molecule, a receptor or a receptor ligand.

The term "nanoparticle" used herein refers to a particle having a diameter of from about 1 to 1000 nm, preferably 1 to 100 nm. Components of the nanoparticle may include metal such as gold, silver, copper, aluminum, nickel, palladium, platinum, alloys thereof, a semiconductor material such as CdSe, CdS, InAs, InP, or core/shell structures thereof, or organic particles such as particles made from organic polymer, lipids, sugars, or other organic materials, e.g. polystyrene, latex, acrylate, or polypeptide. Such organic particles may optionally contain some inorganic material; however, the amount of inorganic material is less than 50%, less than 25%, less than 10%, less than 5%, or less than 1%.

The term "first particle" refers simply to a particle comprised in the microfluidic droplet. "First" does not by itself describe any properties or is linked to any properties unless this is defined specifically by reference to the first particle; it is merely a term distinguishing one particle from further particles.

The term "further particle" refers to another particle which may be identical or different from the first particle and which is comprised in a further microfluidic droplet, preferably a microfluidic droplet defined as the microfluidic droplet of the first aspect, wherein preferably the particle or the potential particle binding partner of the first and the further droplets are different. The term "further particle" can also be understood as "further particle(s)", i.e. it relates to one or more further particles, which are comprised in one or more further microfluidic droplets.

The term "associated" refers to a non-random spatial proximity due to a direct or an indirect interaction. As used herein, the interaction is direct or indirect binding as defined below for the first and the second detectable label, or the binding between particle and potential particle binding partner. It can also mean, for example when the particle is a cell, that the detectable label can be comprised in the particle, e.g. is located within the particle.

The term "detectable label" (or "marker" or "tag") as used herein refers to any kind of substance which is able to indicate the presence of another substance or complex of substances, in particular of a particle or a potential particle binding partner as defined herein, when associated with it. The detectable label can be a substance that is linked to or introduced or incorporated into the substance to be detected. Preferred is a detectable label suitable for allowing for detection and optionally also quantification, e.g. a detectable label emitting a detectable and preferably measurable signal, preferably a light signal. Examples of suitable labels include a dye, a fluorophore, a fluorescent nanoparticle (e.g. quantum dot or lipidot), a chromophore, a radiolabel, a metal colloid, an enzyme (e.g. alkaline phosphatase, luciferase, beta-galactosidase or horseradish peroxidase), or a chemiluminescent or bioluminescent molecule. In the context of the present invention, suitable detectable labels are preferably protein tags whose peptide sequences are genetically grafted into or onto a recombinant protein. Protein tags preferably are fluorescence tags. Fluorescence tags are used to give visual readout on a protein. GFP and its variants (e.g. mutant GFPs having a different fluorescent spectrum) and RFP and its variants (e.g. mutant RFPs having a different fluorescent spectrum) are the most commonly used fluorescence tags. More advanced applications of GFP/RFP include using it as a folding reporter (fluorescent if folded, colorless if not). Further examples of fluorophores include fluorescein, rhodamine, and sulfoindocyanine dye Cy5.

The term "first detectable label" refers to a detectable label that is always associated with the first particle and optionally with a further particle as defined above. The amount of first detectable label associated with the first and optionally a further particle may be known. In case it is only associated with the first particle, i.e. in a case in which there is no further particle, the amount is known. However, the amount of first detectable label associated with the first particle does not need to be known. In this case, the first label is also associated with a further particle as defined above (i.e. the same type of label, as in not the same molecule in the sense that a single first label molecule is attached to each the first and a further particle), wherein the amount of first label associated with the first particle is substantially identical to the amount of first label associated with the further particle, in fact with all further particles. The amount of first detectable label associated with the first and optionally a further particle is not 0.

Preferably, the first detectable label is different from the second detectable label. In particular, if the first and second detectable labels are dyes, especially fluorescent dyes, they differ in their colour, i.e. in the wavelength of light emitted.

In a preferred embodiment, the association of the first particle with the first label is by direct binding or by indirect binding via a linker. "Direct binding" can be a non-covalent binding, but preferably is a covalent binding of the first detectable label to the first particle without a further molecule as an intermediary. "Indirect binding" preferably is a non-covalent (e.g. through biotin-streptavidin interactions) or covalent binding of the first detectable label to the first particle with a further molecule as an intermediary, i.e. with a linker.

The term "second detectable label" refers to a detectable label that is always associated with the potential particle binding partner. In a preferred embodiment, the association of the potential particle binding partner with the second label is by direct binding or by indirect binding via a linker. "Direct binding" preferably is a covalent or non-covalent binding of the second detectable label to the potential particle binding partner without a further molecule as an intermediary. "Indirect binding" preferably is a non-covalent or covalent binding of the second detectable label to the potential particle binding partner with a further molecule as an intermediary, i.e. with a linker. Further, depending on whether particle and potential binding partner bind or not, the second detectable label is also associated with the first particle or not. In a preferred embodiment, the association of the first particle with the second label is by indirect binding via the potential particle binding partner. As such, the association between the particle(s) and the second label depends on whether the potential particle binding partner binds the particle, and the amount of the second label associated with the particle depends on the affinity of the potential binding partner to the particle as well as the number of binding sites if there is more than one binding site on the particle. Preferably, the binding between the potential particle binding partner and the particle is by non-covalent bonds, e.g. by electrostatic interactions, hydrophobic interactions, hydrogen bonds and/or Van der Waals forces. In a preferred embodiment, the binding between the potential particle binding partner and the particle is specific. "Specific binding" as used herein refers to a binding reaction which is determinative of the presence of the binding partner (e.g. the potential particle binding partner or the particle) for example in a situation in which different particles or potential binding partners, which do not specifically bind, are present. Generally, "specifically binds" refers to an equilibrium dissociation constant $K_D$ that is less than about $10^{-5}$ M (e.g., $10^{-6}$ M, $10^{-7}$ M, $10^{-8}$ M, $10^{-9}$ M, $10^{-10}$ M, $10^{-11}$ M, and $10^{-12}$ M or less), preferably at room temperature or at a temperature suitable for maintaining cells, such as about 34-40° C., 35-39° C., 36-38° C. or preferably about 37° C. Methods of how to measure equilibrium dissociation constants are well known in the art. A preferred method uses a BiaCore® system.

In a preferred embodiment, the amount of the second label associated with the first particle may be substantially different from the amount of second label associated with the further particle, wherein "may" means that this is not necessarily so. In a related embodiment, it is substantially different. Both preferably includes the possibility that the amount of the second label associated with the first and/or further particle is 0. While in this case there is no binding between the potential particle binding partner and the particle, the microfluidic droplet still comprises also the potential particle binding partner and the second detectable label. "Substantially different" means not substantially identical as defined herein.

Generally, the idea is that the binding, preferably the amount of binding, of a potential particle binding partner to a first particle can be analyzed. This includes an embodiment wherein all potential binding partners are identical and the particles are different (particle testing/screening), as well as an embodiment wherein the particles are identical and potential binding partners are different (particle binding partner testing/screening). Thus, it is envisaged that in the former embodiment, the potential particle binding partner of the first particle and the potential particle binding partner of the further particle are identical; and in the latter embodiment, the first particle and the further particle are identical.

The term "potential particle binding partner" refers to any type of binding partner, wherein "potential" means that the particle binding partner may or may not bind the particle(s) within the same microfluidic droplet. Preferably, the particle binding partner is selected from the group consisting of an antibody, an antibody derivative, an antibody mimetic, a bacteriophage, an mRNA-polypeptide complex, an mRNA-ribosome-polypeptide complex, a cell, a virus, a peptide, a protein, a nucleic acid, an aptamer and a small molecule.

The term "antibody" refers to both monoclonal and polyclonal antibodies, i.e. any immunoglobulin protein or portion thereof which is capable of recognizing an antigen or hapten. Exemplary antibodies are IgA, IgD, IgE, IgG, IgM, IgY or IgW. In a particular embodiment, the antibody is produced by an antibody-producing cell, e.g. a B cell or a hybridoma cell, within the same microfluidic droplet.

The term "antibody derivative" as used herein refers to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specifically target binding) antibody fragments such as Fab, Fab2, scFv, Fv, or parts thereof, or other derivatives or combinations of the immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent. More preferably, the derivative is a single chain antibody, most preferably having the structure VL-peptide linker-VH or VH-peptide linker-VL.

The term "peptide linker" in this respect refers to a peptide chain of between 1 and 100 amino acids. In preferred embodiments, a peptide linker has a minimum length of at least 1, 2, 3, 4, 5, 6, 7, 8, 9, or 10 amino acids. In further preferred embodiments, a peptide linker according to the present invention has a maximum length of 100, 95, 90, 85, 80, 75, 70, 65, 60, 55, 50, 45, 40, 35, 34, 33, 32, 31, 30, 29, 28, 27, 26, 25, 24, 23, 22, 21, or 20 amino acids. Preferred ranges are 5 to 25 and 10 to 20 amino acids in length. It is preferred that the peptide linker is a flexible peptide linker, i.e. provides flexibility among the domains that are linked together. Such flexibility is generally increased if the amino acids are small and do not have bulky side chains that impede rotation or bending of the amino acid chain. Thus, preferably the peptide linker of the present invention has an increased content of small amino acids, in particular of glycins, alanines, serines, threonines, leucines and isoleucines. Preferably, at least 20%, 30%, 40%, 50%, 60% 70%, 80, 90% or more of the amino acids of the peptide linker are small amino acids. In a preferred embodiment, the amino acids of the linker are selected from glycines and serines, i.e. said linker is a poly-glycine or a poly-glycine/serine linker, wherein "poly" means a proportion of at least 50%, 60% 70%, 80, 90% or even 100% glycine and/or serine residues in the linker. In especially preferred embodiments, the above-indicated preferred minimum and maximum lengths of the peptide linker according to the present invention may be combined.

The term "antibody mimetic" as used herein refers to organic compounds that, like antibodies, can specifically bind antigens, but that are not structurally related to antibodies. They are usually artificial peptides or proteins with a molar mass of about 3 to 20 kDa. Non-limiting examples of antibody mimetics are affibodies, affilins, affimers, affitins, anticalins, avimers, DARPins, fynomers, Kunitz domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, synthetic heterobivalent or heteromultivalent ligands (Josan et al., Bioconjug Chem. 2011 22(7):1270-1278; Xu et al., PNAS 2012 109 (52) 21295-21300; Shallal et al., Bioconjug Chem. 2014 25(2) 393-405) or synthetic or non-synthetic peptide ligands, e.g. from a (random) peptide library. Synthetic peptide ligands have non-naturally occurring amino acid sequences that function to bind a particular target molecule. Peptide ligands within the context of the present invention are generally constrained (that is, having some element of structure as, for example, the presence of amino acids which initiate a β turn or β pleated sheet, or for example, cyclized by the presence of disulfide bonded Cys residues) or unconstrained (linear) amino acid sequences of less than about 50 amino acid residues, and preferably less than about 40 amino acid residues. Of the peptide ligands less than about 40 or 50 amino acid residues, preferred are the peptide ligands of between about 10 and about 30 amino acid residues.

The term "bacteriophage" refers to a virus that infects and replicates in bacteria. In a preferred embodiment, the bacteriophage displays a peptide or protein heterologous (i.e. foreign) to the bacteriophage, which according to the present invention is the potential particle binding partner. This embodiment is based on phage display, which is a technique for studying interactions with peptides or proteins displayed by the bacteriophage. In this technique, a gene encoding a protein of interest is inserted into a phage coat protein gene, causing the phage to display the protein on its outside while containing the gene for the protein on its inside, resulting in a connection between genotype and phenotype. These displaying phages can then be screened against the particle(s), in order to detect interaction between the displayed peptide or protein and the particle(s). In this way, large libraries of peptides or protein can be screened and amplified in a process called in vitro selection. Preferred bacteriophages are M13 phage, fd filamentous phage, T4 phage, T7 phage and lambda phage.

The term "mRNA-polypeptide complex" refers to a complex for mRNA display. mRNA display is a display technique used for in vitro protein and/or peptide evolution to create molecules that can bind to a desired target. The process results in translated peptides or proteins that are associated with their mRNA progenitor via a puromycin linkage. The complex then binds to an immobilized target in a selection step. The mRNA-protein fusions that bind well are then reverse transcribed to cDNA and their sequence amplified via a polymerase chain reaction. The result is a nucleotide sequence that encodes a peptide with high affinity for the molecule of interest. See also Lipovsek and Plückthun, Journal of Immunological Methods 290 (2004) 51-67.

The term "mRNA-ribosome-polypeptide complex" refers to a complex for ribosome display. Ribosome display is a technique used to perform in vitro protein evolution to create proteins that can bind to a desired ligand. The process results in translated proteins that are associated with their mRNA progenitor which is used, as a complex, to bind to an immobilized ligand in a selection step. The mRNA-protein hybrids that bind well are then reversed transcribed to cDNA and their sequence amplified via PCR. The end result is a nucleotide sequence that can be used to create tightly binding proteins. See also Lipovsek and Plückthun, Journal of Immunological Methods 290 (2004) 51-67.

The term "cell" refers to a cell as defined above.

The term virus refers to a small infectious agent replicating only inside living cells of a host organism. Preferably, it is a pathogenic virus, more preferably a virus pathogenic in mammals, in particular humans, e.g. from the class of herpesviridae, adenoviridae, papillomaviridae, polyomaviridae, poxviridae, anelloviridae, parvoviridae, reoviridae, coronaviridae, astroviridae, caliciviridae, flaviviridae, picornaviridae, togaviridae, rhabdoviridae, filoviridae, paramyxoviridae, arenaviridae, bunyaviridae, orthomyxoviridae, retroviridae or hapadnaviridae. Preferably, the potential particle binding partner is not a virus if the particle is a virus.

A protein as a potential particle binding partner may be a natural or a recombinant protein. Preferably, other than proteins defined above such as antibodies, it is a protein displayed or present on the surface of a cell, a receptor or a receptor ligand.

A nucleic acid as a potential particle binding partner may be a natural or a recombinant nucleic acid. Preferred nucleic acids are DNA, RNA and nucleic acid analogues thereof. Nucleic analogues are compounds which are structurally similar to naturally occurring RNA and DNA Nucleic acids are chains of nucleotides, which are composed of three parts: a phosphate backbone, a pucker-shaped pentose sugar, either ribose or deoxyribose, and one of four nucleobases. An analogue may have any of these altered. Typically, the analogue nucleobases confer, possibly among other things, different base pairing and base stacking properties. Examples include universal bases, which can pair with all four canon bases. Nucleic analogues, also termed artificial nucleic acids, include peptide nucleic acid (PNA), Morpholino, locked nucleic acids (LNA), glycol nucleic acid (GNA) and threose nucleic acid (TNA). Each of these is distinguished from naturally occurring DNA or RNA by changes to the backbone of the molecule. A preferred nucleic acid analogue is L-ribonucleic acid aptamer (L-RNA aptamer, trade name Spiegelmer), which is an RNA-like molecule built from L-ribose units. It is a mirror-image of natural oligonucleotides and a form of aptamer. Due to its L-nucleotides, it is highly resistant to degradation by nucleases.

The term "aptamer" refers to an oligonucleotide or peptide molecule that binds to a specific target molecule. Aptamers are usually created by selecting them from a large random sequence pool, but natural aptamers also exist in riboswitches.

The term "small molecules" refers to molecules that have a molecular weight between 50 and about 2,500 Daltons, preferably in the range of 200-800 Daltons. In a preferred embodiment, said small molecule is derived from a library, e.g., a small molecule inhibitor library. Small compound libraries include are plurality of chemical compounds and have been assembled from any of multiple sources, including chemically synthesized molecules and natural products, or have been generated by combinatorial chemistry techniques. They may comprise chemical compounds of a particular structure or compounds of a particular organism such as a plant. Generally, small compounds can be derived or selected from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal cell and tissue extracts can be used. Additionally, test compounds can be synthetically produced using combinatorial chemistry either as individual compounds or as mixtures. A collection of compounds made using combinatorial chemistry is referred to herein as a combinatorial library.

The term "known" encompasses knowledge provided by a third party or determined oneself beforehand.

The term "substantially identical amount" refers to an equivalent amount and does not necessarily mean exactly the same. It is rather determined by what can be considered substantially identical, similar or comparable by the skilled person in view of what is technically feasible when providing the "substantially identical amount". Therein, deviations are normal and acceptable within limits. In a preferred embodiment, the deviation can be up to ±200%, ±100%, ±50%, up to ±40%, up to ±30%, up to ±20% or even only up to ±10% or ±5%, preferably calculated from an arbitrary reference particle such as the first particle, from a particle with the median value of a population of at least three particles (wherein, if the number of particles in the population is even such that two particles could provide the median value, the particle is taken for the median which has the value closed to the average value of the population) or from the average value of a population of at least two particles. Accordingly, instead of the term "substantially identical amount", the term "substantially similar amount" can be used. It is envisaged that if labeling methods do not achieve a desired uniformity, i.e. a substantially identical amount for a population of particles (e.g. of at least two or at least three particles), particles with the desired uniformity, i.e. with a desired amount of label, can be selected from the starting population created by the labeling method, for example with the method of the third aspect of the invention including a step (d) of sorting as described below.

In a particular embodiment, the microfluidic droplet further comprises, associated with an amount of a third detectable label, (i) a particle non-binder or (ii) a second particle not binding the potential particle binding partner.

The term "particle non-binder" or "non-binder to the particle" refers to any type of compound or structure which does not bind the particle(s) within the same microfluidic droplet. Preferably, the particle binding partner is selected from the group consisting of an antibody, an antibody derivative, an antibody mimetic, a bacteriophage, an mRNA-polypeptide complex, an mRNA-ribosome-polypeptide complex, a cell, a virus, a peptide, a protein, a nucleic acid, an aptamer and a small molecule. More preferably, it is of the same type as the potential particle binding partner, i.e. if the potential binding partner is an antibody, the particle non-binder is an antibody, if the potential binding partner is an antibody derivative, the particle non-binder is an antibody derivative, and so on.

The "second particle not binding the potential particle binding partner" or simply the "second particle" is a particle as defined above which is different from the first particle, although it may be of the same type, i.e. if the first particle is a cell, the second particle is also a cell, and if the first particle is a bead, the second particle is also a bead, and so on.

The term "third detectable label" refers to a detectable label that is always associated with the particle non-binder or the second particle, respectively. In a preferred embodiment, the association of the particle non-binder or the second particle, respectively, with the third label is by direct binding or by indirect binding via a linker. "Direct binding" preferably is a covalent or non-covalent binding of the third detectable label to the particle non-binder or the second particle, respectively, without a further molecule as an intermediary. "Indirect binding" preferably is a non-covalent or covalent binding of the third detectable label to the particle non-binder or the second particle, respectively, with a further molecule as an intermediary, i.e. with a linker. Since the particle non-binder does not bind the particle(s) or the second particle does not bind the potential particle binding partner, respectively, the third detectable label is not associated (i) with the first particle or a further particle or (ii) with the potential particle binding partner, respectively. Generally, the third detectable label is different, i.e. distinguishable, from the first and from the second detectable label.

The idea of the use of the particle non-binder or the second particle not binding the potential particle binding partner is the inclusion of a counter-screen as exemplified in Example 4, i.e. the possibility of screening for binding between first particle and potential particle binding partner while at the same time screening against binding between first particle and particle non-binder or between potential particle binding partner and second particle.

Screening for and screening against in this respect may involve sorting the microfluidic droplet for binding between first particle and potential particle binding partner and for no binding between first particle and particle non-binder or between potential particle binding partner and second particle, with the sorting as described herein, in particular with respect to the third aspect of the invention.

In a preferred embodiment, the invention relates to a plurality of microfluidic droplets of the first aspect, wherein either the particles are identical in all microfluidic droplets and the potential particle binding partners are different between the microfluidic droplets, or the potential particle binding partners are identical in all microfluidic droplets and the particles are different between the microfluidic droplets.

In a particular embodiment, each microfluidic droplet of the plurality of microfluidic droplets comprises a particle non-binder or a second particle not binding the potential particle binding partner.

The term "population" or "plurality" means "more than one". In preferred embodiments, it means more than 10, more than 20, more than 30, more than 40, more than 50, more than 100, more than 250, more than 500 or more than 1000.

In a second aspect, the present invention relates to a method for quantifying the binding between a particle and a potential particle binding partner in a microfluidic droplet according to the first aspect, comprising the steps of
(i) measuring the signal determining of the first detectable label,
(ii) measuring the signal of the second detectable label, and
(iii) normalizing the signal of the second detectable label using the signal of the first detectable label,
wherein the normalized signal of the second detectable label represents the quantity of binding between a particle and a potential particle binding partner.

All terms have the meanings as defined above and embodiments defined related to these terms also apply to the method of the second aspect.

In a particular embodiment, said method is for quantifying the binding between a particle and a particle binding partner in a microfluidic droplet according to the first aspect, comprising the steps of
(i) measuring the signal of the first detectable label,
(ii) measuring the signal of the second detectable label, and
(iii) normalizing the signal of the second detectable label using the signal of the first detectable label,
wherein the normalized signal of the second detectable label represents the quantity of binding between a particle and a particle binding partner.

Preferably, the signal of the second detectable label is measured at the same location within the microfluidic droplet as the signal of the first detectable label, more preferably at the same time, i.e. simultaneously.

"Measuring the signal" refers to measuring the strength of signal or the intensity of the signal of the detectable label at any position within the droplet, i.e. not necessarily at the position of the label within the droplet. The strength of the signal varies within the droplet depending on the position of the detectable label, but the measurement at any (including another) position is compensated by the use of two detectable labels, i.e. the first and the second label, and the normalization step. This normalization step allows for quantifying the binding irrespective of the position of the labels within the droplet and of the position where the signal is measured, as long as the signal of all labels is measured at the same position, see FIG. 5. The means for detecting depends on the detectable label used. Preferably, the detectable label emits a light signal. Light signals can, for example, be measured by lights sensors, e.g. photomultiplier tubes, CMOS or CCD cameras. If the detectable label is excitable, the step of determining the amount can include an excitation step, for example with a laser light source. In a preferred embodiment, the signal is laser-induced fluorescence and the signal is detected, i.e. the amount is determined, by laser spectroscopy.

"Normalizing" as used herein refers to adjusting the value for the signal of the first detectable label of step (i) with the value for the signal of the first detectable label of step (ii). In principle, any adjustment serves normalization, for example adjustment by any mathematical operation such as addition, subtraction, multiplication, division or any combination thereof. In a preferred embodiment, step (iii) comprises dividing the value for the signal of the second label by the value for the signal of the first label.

In another preferred embodiment, step (iii) further comprises normalizing the signal of the second label by subtracting the second detectable label background, preferably in addition to above dividing, more preferably before the dividing. The second detectable label background is the signal of the second detectable label which is not associated with the particle. It can be determined, for example, at a location in the microfluidic droplet where the signal of first detectable label is 0 or minimal within the microfluidic droplet. Alternatively, it is the signal of second label in a control microfluidic droplet, which can be empty (i.e. comprising at least no detectable labels or even no particle and no potential particle binding partner) or which differs from the microfluidic droplet according to the first aspect only in that the second label is not associated with the first particle in the control microfluidic droplet, i.e. in that the potential particle binding partner to which the second label is bound does not specifically bind the particle, or in that the first particle is not present in the control microfluidic droplet.

In a particular embodiment, the method of the second aspect comprises a step (iv) of measuring the signal of a third detectable label associated with a particle non-binder or a second particle not binding to the potential particle binding partner, as defined above.

In a third aspect, the present invention relates to a method for detecting one or more particles comprised in a microfluidic droplet, comprising the steps of:
(a) feeding a microfluidic droplet comprising one or more particles into a detection channel comprising a detection point,
(b) constricting at least the vertical movement of the particle (s) within the microfluidic droplet at least at the detection point in the detection channel, compared to the same microfluidic droplet when having a spherical shape, and
(c) detecting at least one particle comprised in the microfluidic droplet at the detection point.

The term "channel" can mean a recess or cavity formed in a material by imparting a pattern into a material or by any suitable material removing technique, or can mean a recess or cavity in combination with any suitable fluid-conducting structure mounted in the recess or cavity, such as a tube, capillary, or the like. Generally, it refers to a microchannel of a diameter of 3000 µm or less, 2000 µm or less, 1000 µm or less, preferably 900, 800, 700, 600, 500, 400, 300, 200, 150, 100, 50 nm or less, preferably the diameter is between 20 nm and 3000 µm, preferably between 20 nm and 1000 µm and more preferably between 20 nm and 100 µm. In a preferred embodiment, the channel is part of a microfluidics network. If the channel does not have a circular cross-section, the height and/or width of the channel is/are according to the sizes given for the diameter above.

Several types of channels are described herein, such as a feed channel, a detection channel, a sorting channel and branch channels. These terms do not necessarily demarcate one channel type from another, since these terms describe partly channel sections the borders of which are not in all instances defined. For example, the feed channel merges with the detection channel downstream thereof, and the detection channel merges with the sorting channel downstream thereof. A clear demarcation is only the sorting junction, which is where the sorting channel ends and the branch channels begin. Otherwise, channels or channel sections can be distinguished by their height and optionally width as defined below or by other features they possess, such as a detection point, a sorting means etc.

The term "detection channel" refers to a channel or part of a channel where microfluidic droplets or its contents can be detected at a "detection point". Preferably, one or more, more preferably all walls of the detection channel are transparent at least at the detection point.

The term "vertical movement" refers to the movement of the particle(s) or the space for movement within the microfluidic droplet in the direction of or opposite of gravity when the detection channel and particularly a microfluidic device (e.g. chip) comprising the detection channel is in its intended spatial orientation or position, e.g. lying flat on a horizontal area.

"Constricting" the vertical movement refers to a reduction of the vertical movement or the space for movement of the particle within the microfluidic droplet. This can be achieved, for example, by confinement of the vertical space within the droplet in which the particle(s) can move, i.e. by deforming the droplet resulting in a reduced vertical space. In a preferred embodiment, the height of the detection channel is smaller at least at the detection point than the diameter of the droplet when in spherical shape, i.e. reduced channel height leads to a deformation of the droplet resulting in a reduced vertical space. In another embodiment, electrodes below or above the detection channel, preferably at the detection point, can pull the droplet to the bottom or top of the channel by applying AC voltages with a force sufficient to deform the droplet resulting in a reduced vertical space within the droplet.

In a preferred embodiment, step (b) comprises constricting also the horizontal movement of the particle(s) within the microfluidic droplet at least at the detection point in the detection channel, compared to the same microfluidic droplet when having a spherical shape. The term "horizontal movement" refers to the movement in a 90° angle to the vertical movement as defined above. This can be achieved, for example, by confinement of the horizontal space within the droplet in which the particle(s) can move, i.e. by deforming the droplet resulting in a reduced horizontal space. In a preferred embodiment, the width of the detection channel is smaller at least at the detection point than the diameter of the droplet when in spherical shape, i.e. reduced channel width leads to a deformation of the droplet resulting in a reduced horizontal space. In another embodiment, electrodes on one side of the detection channel, preferably at the detection point, can pull the droplet to the side of the channel by applying AC voltages with a force sufficient to deform the droplet resulting in a reduced horizontal space.

Accordingly, in a preferred embodiment, the vertical movement and optionally also the horizontal movement of the particle(s) is constricted by channel height and optionally width and/or by dielectrophoresis. In the former case (height and width constriction), the microfluidic droplet forms a plug in the detection channel at least at the detection point, i.e. it fills the cross-section of the channel and no more than a thin film of the fluid (the immiscible liquid) surrounds the microfluidic droplet.

The term "spherical shape" refers to a shape of the droplet not confined in space and when it is not moving. Preferably, the diameter of a spherical droplet is uniform, i.e. the same at any point, with a deviation of up to 1, 2, 3, 4, 5 or up to 10%.

The term "detecting" a particle refers to determining the presence or absence of the particle. In a preferred embodiment, a particle is detected via detecting a label associated with the particle, such as a first label as defined above. Detection means are well known in the art and include the means indicated above, e.g. lights sensors, for example photomultiplier tubes, CMOS or CCD cameras, or detection electrodes. Generally, the detection means is suitable for detecting a particle and/or a label microfluidic droplet as defined herein. In particular with respect to the label, the detection means is suitable for measuring the strength of the signal of a label, and preferably for measuring the signal of a label. Thus, in a preferred embodiment, the detection means detects a label associated with the one or more particles and optionally the detection means measures the signal of the label associated with the one or more particles.

In a particularly preferred embodiment, the detecting in step (c) comprises a quantification according to the method of the second aspect.

In one embodiment, the microfluidic droplet is fed into the detection channel in step (a) through a feed channel upstream of the detection channel, characterized in that the height and width of the feed channel are such that the vertical and horizontal movement of the particle(s) within the microfluidic droplet are not constricted, i.e. such that the microfluidic droplet has a spherical shape. In particular, the microfluidic droplet does not form a plug in the feed channel. The term "feed channel" refers to a channel that delivers fluids and microfluidic droplets therein to the detection channel.

In a preferred embodiment, the detection and feed channel are characterized in that the height and optionally the width of the detection channel at least at the detection point is less than 100, 90, 70, 60, 50, 40, 30, 20 or less than 10% of the height and optionally width of the feed channel. Preferably, the height and optionally width of the detection channel at least at the detection point is between 20 and 50 μm, preferably between 30 and 40 μm, and/or the height and optionally width of the feed channel is between 50 and 3000 μm, preferably between 100 and 1000 μm.

Also, the detection channel can be characterized in that the height and optionally the width of the detection channel at least at the detection point is less than 100, 90, 70, 60, 50, 40, 30, 20 or less than 10% of the average height and optionally average width of all channels comprised in the same microfluidic device as the detection channel. Preferably, the height and optionally width of the detection channel at least at the detection point is between 20 and 50 μm, preferably between 30 and 40 μm, and/or the average height and optionally average width of all channels comprised in the same microfluidic device as the detection channel is between 50 and 3000 μm, preferably between 100 and 1000 μm.

In a preferred embodiment, the method of the third aspect further comprises a step (d) of sorting the microfluidic droplet based on the detection of the particle(s), in particular based on the signal of the detected particle(s), in a sorting channel downstream of the detection channel, preferably at a sorting junction at the end of the sorting channel.

The term "sorting" refers to selecting or separating a microfluidic droplet based on its properties, preferably based on its contents, including the presence or absence of one or more particles, potential particle binding partners and/or particles bound to potential particle binding partners as described above. How these contents can be detected is also described above.

The term "sorting channel" refers to a channel or part of a channel where microfluidic droplets can be sorted using a sorting means such as a sorting divider, i.e. the sorting channel preferably comprises a sorting divider. The term "sorting divider" refers to a channel geometry comprising a sorting channel having a sorting junction, where the sorting channel branches out into at least 2, 3, 4, 5, 6, 7, 8, 9 or at least 10 branch channels. Associated with the sorting divider is usually a sorting force or manipulation means, which can be based on dielectrophoresis (X. Hu et al., Marker-specific sorting of rare cells using dielectrophoresis. Proc Natl Acad Sci USA 102, 15757 (Nov. 1, 2005), valves (A. Y. Fu, C.

Spence, A. Scherer, F. H. Arnold, S. R. Quake, A microfabricated fluorescence-activated cell sorter. Nat Biotechnol 17, 1109 (November, 1999)), optics (Z. C. Landry, S. J. Giovanonni, S. R. Quake, P. C. Blainey, Optofluidic cell selection from complex microbial communities for single-genome analysis. Methods in enzymology 531, 61 (2013)), acoustics (L. Schmid, D. A. Weitz, T. Franke, Sorting drops and cells with acoustics: acoustic microfluidic fluorescence-activated cell sorter. Lab on a Chip 14, 3710 (Oct. 7, 2014)) or stream deflection, preferably electric stream deflection (P. S. Dittrich, P. Schwille, An integrated microfluidic system for reaction, high-sensitivity detection, Anal Chem.; 75 (21): 5767-74. (2003)).

Accordingly, the sorting divider may be a DEP sorting divider, an acoustophoresis sorting divider, a microvalve-based sorting divider, a piezoelectric sorting divider, or a dynamic stream deflection sorting divider. Preferred is a DEP sorting divider. In a particular embodiment, the DEP sorting divider is an optically induced dielectrophoretic (ODEP) sorting divider.

Thus, with respect to the embodiment comprising the further step (d), the sorting channel preferably comprises a sorting divider comprising a sorting junction where the sorting channel branches out into at least two branch channels. In a more preferred embodiment, the sorting channel further comprises a droplet manipulation means, preferably selected from means described above, more preferably a dielectrophoretic (DEP) force manipulation means.

In a preferred embodiment, height and width of the sorting channel and preferably also of the branch channels are such that the vertical and horizontal movement of the particle(s) within the microfluidic droplet is not constricted, i.e. such that the microfluidic droplet has a spherical shape. In particular, the microfluidic droplet does not form a plug in the sorting channel and preferably also in the branch channels.

In a preferred embodiment, the detection and sorting channel (preferably also the branch channels) are characterized in that the height and optionally the width of the detection channel at least at the detection point is less than 100, 90, 70, 60, 50, 40, 30, 20 or less than 10% of the height and optionally width of the sorting channel (preferably also of the branch channels). Preferably, the height and optionally width of the detection channel at least at the detection point is between 20 and 50 μm, preferably between 30 and 40 μm, and/or the height and optionally width of the sorting channel (preferably also of the branch channels) is between 50 and 3000 μm, preferably between 100 and 1000 μm.

In a particular embodiment A, the method of the third aspect further comprises monitoring both the detecting and the sorting of the microfluidic droplet using an objective with a magnification of at least 20×, preferably of at least 30×, more preferably of at least 40× or even of at least 50× (i.e. within the same field of view of the objective). Preferably, this detecting and the sorting is done using a microscope having said objective. For this embodiment, it is advantageous that the distance between the detection point and the sorting junction is 500 μm or less, 400 μm or less, 300 μm or less, 200 μm or less, or 100 μm or less, wherein the minimal distance in each case is at least 50 μm. Preferably, independent of or including the afore-mentioned limitation, the distance is less than 10×, 9×, 8×, 7×, 6×, 5× or even 3× of the diameter of the microfluidic droplet in spherical form. In this respect, the term "distance" does not refer to distance a droplet travels in the channel, but to the shortest spatial distance between the points irrespective of the channel route.

In a particular embodiment B, which is combinable with embodiment A, the sorting and/or detection channel is kinked or has a bend, both in the sense of not being straight, downstream of the detection point of the detection channel and upstream of the sorting junction. "Kinked" or "having a bend" in this respect preferably means having a sideway (i.e. to the left or right from a top view) angle of at least 5°, 10°, 20°, 30°, 40°, 45°, 50°, 60°, 70°, 80° or 90°, preferably 10° to 90°, more preferably 10° to 45°. This advantageously contributes to achieving a short distance between the detection point and the sorting junction.

In a particular embodiment C, which is combinable with embodiment A and/or B, the method of the third aspect further comprises injecting fluid into the sorting channel through fluid inlets upstream of the sorting junction, thereby controlling passing droplets, to facilitate sorting. This means (here and in corresponding embodiments herein) that the fluid is injected downstream of the detection point of the detection channel and that the corresponding fluid inlets are downstream of the detection point and upstream of the sorting junction. "Controlling passing droplets" preferably means spacing them out to a minimal or defined distance from each other and/or to focus them near the sorting junction. In a preferred embodiment, the droplets are spaced out such that the distance between two consecutive droplets is at least 10 times, 8 times, 6 times, 4 times or 2 times the droplet diameter. Focusing the droplets near the sorting junction means focusing by additional fluid inlets to adjust the trajectory of the droplets such that in absence of any droplet manipulation by means as described above (such as DEP, valves, etc.) passing droplets end up in a waste channel, i.e. a channel into which droplets showing an undesired phenotype are flushed. The waste channel is preferably one of the at least two branch channels.

In a preferred embodiment, all droplets, irrespective of the detection and/or the sorting decision, are controlled in the same manner, i.e. the controlling is not a sorting. This embodiment has the advantage that only minimal and/or uniform pulses are required for the sorting, i.e. to nudge the droplets into a branch channel at the sorting junction or even upstream of the sorting junction, and that the strength of the pulses do not have to be adjusted by varying locations of the droplets within the channel. Preferably, the controlling of the droplet is based on information from the detection means described herein and/or a (possibly additional) camera or detection electrode(s) regarding the position of the droplet in the channel (in particular in the sorting channel), preferably regarding its distance from the channel walls, the distance from the sorting divider and/or the distance or time between detections regarding the preceding droplet.

In a preferred embodiment of the method of the third aspect, the particles are cells and the microfluidic droplet is sorted for comprising cells of two different cell types, preferably two different single cells, e.g. an antibody-producing cell and a reporter cell signaling, preferably by fluorescence, the effect of the antibody produced by the antibody-producing cell on the reporter cell (e.g. the activation or inhibition of a receptor, preferably a G-protein coupled receptor). In this embodiment, the two different cell types, preferably the two different single cells, carry different detectable labels. In other words, in this preferred embodiment, the microfluidic droplet comprises one or more different particles which are cells of different cell types each associated with a different detectable label, preferably fluorescent label, and the cells are detected via the detectable label in step (c) and the microfluidic droplet is sorted for comprising at least two different cells, preferably at least two different single cells, of different cell types in step (d)

In another preferred embodiment of the method of the third aspect, the microfluidic droplet comprises a particle that is a cell or a bead coated with antigen and a potential particle binding partner as defined above, e.g. an antibody, antibody derivative or antibody mimetic, and the microfluidic droplet is sorted for binding of a certain amount, e.g. a certain minimal amount, of binding between particle and potential particle binding partner.

In a particular embodiment, the method of the third step comprises, after the step (d) of sorting, a step (e) of identifying or analyzing the particle and/or potential particle binding partner (or source thereof if the potential particle binding partner is produced in the microfluidic droplet, e.g. an antibody produces by a B-cell or a hybridoma cell) in one or more microfluidic droplets sorted for. This allows determining which particle binds which potential particle binding partner. For example, if the potential particle binding partner is an antibody, the antibody-encoding genes of the corresponding B-cell or hybridoma can be amplified by RT-PCR and sequenced to obtain structural information about the antibody.

In a fourth aspect, the present invention relates to a population of microfluidic droplets, wherein more than 50%, preferably more than 60%, 70%, or 80%, more preferably more than 90% or even more than 95% of the microfluidic droplets comprise each a single particle of at least two types, especially a single cell of at least two cell types. Such high percentages can be achieved with the method of the third aspect including a sorting step, but not by non-deterministic or even deterministic encapsulation of two or more single particles or cells of different types. Thus, in a preferred embodiment, said population is produced using the method of the third aspect further comprising a step (d) of sorting as described above, preferably in combination with the feature of one or more of embodiments A, B and/or C described above. In this method, to achieve said population, the microfluidic droplets are sorted for comprising a single particle or cell of at least two types.

In a fifth aspect, the present invention relates to a microfluidic device for detecting one or more particles comprised in a microfluidic droplet, comprising a detection channel with a detection point, characterized in that the device is designed such that at least the vertical movement of the particle(s) within the microfluidic droplet is constricted in the detection channel at least at the detection point, compared to the same microfluidic droplet when having a spherical shape.

In a preferred embodiment, the device is designed such that also the horizontal movement of the particle(s) within the microfluidic droplet is constricted in the detection channel at least at the detection point, compared to the same microfluidic droplet when having a spherical shape.

As used herein, the term "microfluidic device" generally refers to a device through which materials, particularly fluid borne materials, such as liquids, can be transported, in some embodiments on a micro-scale, and in some embodiments on a nanoscale. Thus, the microfluidic devices can comprise microscale features, nanoscale features, and combinations thereof.

In the context of the invention, the term also refers to a) a device that comprises a plurality of enclosed microchannel structures, each of which comprises one or more enclosed microchannels and/or microcavities, and b) that these microchannel structures are used for transporting and processing liquid aliquots, in particular microfluidic droplets as described above, that are in the nano- to microliter range and may contain reactants including e.g., analytes and reagents. The liquid aliquots are typically aqueous. The transporting and processing are typically part of an analytically and/or a preparative process protocol. The number of microchannel structures in a device may be more than 1, 2, 3, 4, 5, 10, 25 or 50 and is typically below 500, for example below 100.

An exemplary microfluidic device typically comprises structural or functional features dimensioned in the order of a millimeter-scale or less, which are capable of manipulating a fluid at a flow rate on the order of several hundred μL/hr or less. Typically, such features include, but are not limited to channels, fluid reservoirs, reaction chambers, mixing chambers, and separation regions. In some examples, the channels include at least one cross-sectional dimension that is in a range of from about 20 μm to about 3000 μm, preferably to about 1000 μm. The use of dimensions in this order allows the incorporation of a greater number of channels in a smaller area, and utilizes smaller volumes of fluids.

In a preferred embodiment, the microfluidic device is a microfluidic chip. As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 $mm^2$ to about 0.25 $m^2$. Preferably, the size of the chips is from about 4 $mm^2$ to about 50 $cm^2$ with a characteristic dimension from about 1 mm to about 5 cm. The chip surfaces may be flat, or not flat. The chips with non-flat surfaces may include channels or wells fabricated on the surfaces.

Preferably, the microfluidic device and in particular the microfluidic chip is made of an optically transparent polymer or of glass. A particularly preferred transparent polymer is poly(dimethylsiloxane) (PDMS). PDMS chips can be fabricated, for example, by soft lithography (Squires and Quake. Microfluidics: Fluid physics at the nanoliter scale. Reviews of Modern Physics, 2005, vol. 77). Other suitable polymers are, for example, Ormocomp, polymethylmethacrylate (PMMA), Sifel, cyclo-olefin copolymer (COC), polyvinylidene fluoride (PVDF) or polystyrene (PS).

The term "designed such that . . . " refers to features relating to constricting movement as described above for the method of the third aspect. Preferably, it refers to the vertical movement and optionally also horizontal movement of the particle(s) being constricted by channel height and optionally width and/or by dielectrophoresis.

In a further embodiment, the device of the fifth aspect comprises one or more of
(i) a feed channel upstream of the detection channel,
(ii) a sorting channel downstream of the detection channel, and/or
(iii) at least two branch channels,
all as described above.

Apart from the features described with respect to the above aspects of the invention, the device of the fifth aspect may also comprise one or more integrated electrodes, microvalves, micropumps droplet generators and/or a laser spectroscopy setup. "Integrated" means embedded between two layers of device material as specified above (e.g. glass or PDMS) or placed on top of the device, preferably a chip.

Generally, electrodes can enable on-chip functionalities such as electrical impedance spectrometry, electrophoresis, amperometric detection, temperature sensing, electrical heating (e.g. to provide a temperature suitable for maintaining cells, such as about 34-40° C., 35-39° C., 36-38° C. or preferably about 37° C.), generating electroosmotic flow and/or high voltage microfluidic experimentation. Exemplary electrodes are field electrodes, detection electrodes, and heating and sensing electrodes. Field electrodes are used to conduct electrical current and generate electrical fields for controlling electroosmotic flows. Detection electrodes are used to measure the local electrical conductivity or impedance of the liquid in a fluidic channel. Detection electrodes can in particular be used for example to count and characterize particles, especially cells, in microfluidic droplets. Heating and sensing electrodes are used as electrical heaters and temperature sensors on a chip to provide a convenient means to heat fluids inside microchannels and measure the temperature. This is particularly useful if the microfluidic droplets contain cells, i.e. if the particles of the aspects of the invention are cells. While heating and sensing electrodes can be used independently from each other, i.e. while the device can comprise heating or sensing electrodes, it is preferred that it comprises both and even more preferred that they are functionally coupled and that the heating electrodes are controlled by a feedback loop according to temperatures measured with the sensing electrodes such that a desired temperature is maintained, in particular a temperature suitable for maintaining cells as described above. Between electrodes and microfluidic channels, insulating layers can be applied.

As used herein, the term "microvalve" generally relates to a valve which, with respect to fluids, can selectively be brought into one of two distinct states: a valve open state in which fluid can pass through the valve and a valve closed state in which fluid is blocked to pass the valve. Microvalves control routing, timing, and separation of fluids within a microfluidic device. Generally, microvalves can be actuated mechanically, pneumatically, electrokinetically, by phase changes, or by introduction of external force. Accordingly, the microvalves can be independently selected (i.e. the device may contain different microvalves) from the group consisting of electrokinetic microvalves, pneumatic microvalves, pinch microvalves, phase change microvalves, burst microvalves and Braille pin pinch microvalves. Preferably, the microvalves are independently selected from the group consisting of pneumatic microvalves and Braille pin pinch microvalves, phase change microvalves, and burst microvalves. Electrokinetic microvalves operate in continuous flow systems, serving as a fluid router that uses electroosmotic flow to switch fluids from one channel to another. Pneumatic microvalves typically rely on a flexible membrane to control the flow pattern in the flow channel. Pinch microvalves operate by physically deforming the device material as defined above, e.g. PDMS, using mechanical pressure. Phase-change microvalves alternate between different phases of materials such as paraffin, hydrogels, or aqueous solutions to modulate flow. Burst microvalves are single-use valves that are opened when a flow resistance is overcome or when a sacrificial membrane is disintegrated. Lastly, Braille pin pinch microvalves generate localized pressure via the mechanical pins of Braille displays, which are normally used to communicate with the blind and represent an inexpensive and easily programmable valve control method. The pinching points may but do not need to be the valving points. In case of the latter, each pin presses onto a liquid-filled reservoir, which acts as a piston that transmits the pressure to a membrane-based pneumatic valve.

The term "micropump", as used herein, refers to a structure that can provide force for displacement of liquids or gases within a microchannel. A wide variety of pumping mechanisms are known in the art. Preferably, the "micropump" is of a positive displacement type wherein the pump generates a positive pressure, above the atmospheric pressure, and the higher pressure is coupled to at least one microfluidic channel. The differential pressure causes movement of the gas or liquid. An "integrated micropump", also known as "integrated pressure source", "on-chip micropump" or "on-chip pressure source", refers to a micropump configuration that is an integral part of the microfluidic device and is preferably irreversibly attached to it. Thus, in the microfluidic device of the invention, micropumps are responsible for generating temporal and volumetric fluid movement and are used to reduce the amount of external hardware necessary to operate the microfluidic device. Generally, a micropump is active or passive. Passive micropumps rely for example on the phenomenon that small fluid volumes in contact with microstructured surfaces move spontaneously as a result of the interplay between the liquid's surface tension and the surface's chemical composition and topography in the direction that minimizes the free energies between the vapor, fluid, and solid interfaces. Alternatively, they can rely on the surface tension of droplets placed at inlets/outlets of microchannels to drive the flow. Therein, the flow rates are dictated by the curvature of the droplets, which in turn are controlled by the amount of fluid dispensed. Preferred, however, are active micropumps since they are amenable to computerized control. Active micropumps rely on an external signal to initiate and cease pumping activities. This external signal adds the ability to control the rate and temporal behavior of the pump. Preferably, the active micropumps are independently selected (i.e. the device may contain different micropumps) from the group consisting of syringe micropumps, pneumatic membrane micropumps, piezoelectric micropumps, Braille pin micropumps, electrochemical micropumps, electroosmotic micropumps, acoustic micropumps, magnetohydrodynamic micropumps, electrohydrodynamic micropumps and gas permeation micropumps; more preferably, the active micropumps are independently selected from the group consisting of syringe micropumps, pneumatic membrane micropumps and Braille pin micropumps.

Syringe micropumps are pumping devices including a syringe, i.e. a barrel, housing or similar structure that defines a cavity, chamber, or similar structure in which a piston, plunger or similar structure is slidable so as to eject a fluid there. A syringe pump allows for precise actuation of the fluids. Pneumatic membrane micropumps are generally based on an existing microvalve design with several such valves actuating in series to produce peristalsis in the microchannel. Briefly, a fluid volume ("bolus") is bound between activated pumping membranes and moves unidirectionally through sequential activation of the pumping membranes. Consequently, the bolus will move away from its initial position, generating a volume displacement in the microchannel. Piezoelectric micropumps rely on a piezoelectric device material undergoing shape changes when supplied with an electrical current. Stress exerted by the piezoelectric material, coupled to a (preferably thin) diaphragm, can be used to pump fluids. Braille pin micropumps are operated using the push-pins of a Braille display, which are programmed to operate in a peristaltic pattern. Electrochemical micropumps use gas generated from the electrolysis of an aqueous solution of e.g. $KNO_3$ to pump fluid through a microchannel. By adjusting the current amplitude and pulse using electrodes connected to a microchannel, a flow can be achieved. Electroosmotic micropumps rely on electroosmotic flow, which is the bulk motion of liquid resulting from an applied electric field across a porous material, capillary, membrane, or microchannel with charged walls. When for example a DC electric field is applied across at least two electrodes, a high force is experienced at the microchannel walls, resulting in the movement of charge and fluid through the microchannel. Acoustic micropumps rely on acoustic streaming, which refers to the phenomenon that (i) compressible fluid experiences a high-frequency oscillation driven by a source of sound, wherein the nonlinear interaction causes a steady current or (ii) incompressible fluid oscillates adjacent to an obstacle or an interface. In particular, acoustic streaming flows based on quartz wind, Eulerian streaming and Kundt's dust are suitable for microfluidic devices (see Suh and Kang on Acoustic Separation in "Encyclopedia of Microfluidics and Nanofluidics", Springer Reference, Volume 1, pages 25 to 32). Magnetohydrodynamic micropumps drive fluid flow in conductive liquids which are subjected to perpendicular applied electric and magnetic fields across a microchannel. A resulting Lorentz force is generated on the liquid perpendicular to the direction of both the electric and magnetic fields, therefore causing the fluid to be pumped through the microchannel. Electrohydrodynamic micropumps use electrowetting to manipulate discrete droplets of fluid over an array of electrodes in what is known as digital microfluidics. Electrowetting is the change in contact angle between a solid and electrolyte resulting from the application of an electric field between the two. Gas permeation micropumps operate with gas permeable microfluidic device materials, such as PDMS. The working principle is that the removal of all the residual gas that is present in the gaspermeable material (e.g. by placing the device in vacuum for 15-20 min) will create a local vacuum in the microchannels, which can pull fluid through the channels. For a review of the above microvalves and micropumps, see Au et al., Micromachines 2011, 2, 179-220.

The term "droplet generator" refers to a structure creating a stream of monodispersed water or oil droplets in an immiscible phase. Microfluidic droplet generators work by combining two or more streams of immiscible fluids and generating a shear force on the discontinuous phase causing it to break up into discrete droplets. Preferred droplet generators are focused-flow droplet generators and T-shaped droplet generators. Focused-flow droplet generators are based on a continuous phase fluid (focusing or sheath fluid) flanking or surrounding the dispersed phase (focused or core fluid), so as to give rise to droplet break-off in the vicinity of an orifice through which both fluids are extruded. T-shaped droplet generators use a microchannel T-junction, at which droplets are spontaneously formed at the intersection, taking advantage of the interface instability between oil and aqueous streams each coming from one direction towards the junction. For other methods of generating droplets, see the compartmentalisation or microencapsulation procedures described above.

In a particular embodiment A, the device further comprises, downstream of the detection channel, a sorting channel for separating microfluidic droplets based on the signal of the detected particle(s), wherein the distance between the sorting divider and the detection point is 500 µm or less, preferably less than 10×, 9×, 8×, 7×, 6×, 5× or even 3× of the diameter of the microfluidic droplet in spherical form. In this respect, the term "distance" does not refer to the distance a droplet travels in the channel, but to the shortest spatial distance between the points irrespective of the channel route. This embodiment has the advantage that both the detecting and the sorting of microfluidic droplets can be monitored more easily using an objective with a magnification of at least 20×, preferably of at least 30×, more preferably of at least 40× or even of at least 50× (i.e. within the same field of view of the objective). Preferably, this detecting and the sorting is done using a microscope having said objective.

In a particular embodiment B, which is combinable with embodiment A, the sorting and/or detection channel of the device is kinked or has a bend as described above. This advantageously contributes to achieving a short distance between the detection point and the sorting junction.

In a particular embodiment C, which is combinable with embodiment A and/or B, the device further comprises one or more fluid inlets upstream of the sorting junction and downstream of the detection point for injecting fluid into the sorting channel. The injection of fluid is for controlling passing droplets, to facilitate sorting. "Controlling passing droplets" preferably means spacing them out to a minimal or defined distance from each other and/or to focusing them near the sorting junction. In a preferred embodiment, the droplets are spaced out such that the distance between two consecutive droplets is at least 10 times, 8 times, 6 times, 4 times or 2 times the droplet diameter. Focusing the droplets near the sorting junction means focusing by additional fluid inlets to adjust the trajectory of the droplets such that in absence of any droplet manipulation by means as described above (such as DEP, valves, etc.) passing droplets end up in a waste channel, i.e. a channel into which droplets showing an undesired phenotype are flushed. The waste channel is preferably one of the at least two branch channels.

In a preferred embodiment, the one or more fluid inlets are governed such that all droplets, irrespective of the detection and/or the sorting decision, are controlled in the same manner, i.e. the controlling it not a sorting. This has the advantage that only minimal pulses are required for the sorting, i.e. to nudge the droplets into a branch channel at the sorting junction or even upstream of the sorting junction. The term "governed" means controlled and is used merely to avoid confusion with controlling of the droplets. Preferably, the fluid inlets are governed by a control means, such as a CPU, which receives information from the detection means described herein and/or a (possibly additional) camera regarding the position of the droplet in the channel (in particular in the sorting channel), preferably regarding its distance from the channel walls.

The additional device features of each of embodiments A, B and C described above are each advantageous for the methods of the invention by themselves, i.e. without the characterizing device feature of the device of the fifth aspect, namely without the feature that the device is designed such that at least the vertical movement of the particle(s) within the microfluidic droplet is constricted in the detection channel at least at the detection point, compared to the same microfluidic droplet when having a spherical shape.

Accordingly, in a sixth aspect, the present invention relates to a microfluidic device for detecting one or more particles comprised in a microfluidic droplet, comprising a detection channel with a detection point, characterized in that it comprises, downstream of the detection channel, a sorting channel with a sorting junction for separating microfluidic droplets based on the signal of the detected particle(s), wherein the distance between the sorting junction and the detection point is 500 µm or less (as specified above), preferably less than 10×, 9×, 8×, 7×, 6×, 5× or even 3× of the diameter of the microfluidic droplet in spherical form.

Preferably, this microfluidic device is further characterized by one or more of the following:

(i) the device is designed such that at least the vertical movement of the particle(s) within the microfluidic droplet is constricted in the detection channel at least at the detection point, compared to the same microfluidic droplet when having a spherical shape, (ii) the sorting and/or detection channel of the device is kinked or has a bend as described above, and/or (iii) the device further comprises one or more fluid inlets upstream of the sorting junction and downstream of the detection point for injecting fluid into the sorting channel.

The device of the sixth aspect can be modified further as described for the device of the fifth aspect of the invention.

Further, in a seventh aspect, the present invention relates to a microfluidic device for detecting one or more particles comprised in a microfluidic droplet, comprising a detection channel with a detection point, characterized in that it comprises, downstream of the detection channel, a sorting channel with a sorting junction for separating microfluidic droplets based on the signal of the detected particle(s), wherein the sorting and/or detection channel of the device is kinked or has a bend as described above.

Preferably, this microfluidic device is further characterized by one or more of the following:

(i) the device is designed such that at least the vertical movement of the particle(s) within the microfluidic droplet is constricted in the detection channel at least at the detection point, compared to the same microfluidic droplet when having a spherical shape, (ii) wherein the distance between the sorting junction and the detection point is 500 µm or less (as specified above), preferably less than 10×, 9×, 8×, 7×, 6×, 5× or even 3× of the diameter of the microfluidic droplet in spherical form, and/or (iii) the device further comprises one or more fluid inlets upstream of the sorting junction and downstream of the detection point for injecting fluid into the sorting channel.

The device of the seventh can be modified further as described for the device of the fifth aspect of the invention.

Further, in an eighth aspect, the present invention relates to a microfluidic device for detecting one or more particles comprised in a microfluidic droplet, comprising a detection channel with a detection point, characterized in that it comprises, downstream of the detection channel, a sorting channel with a sorting junction for separating microfluidic droplets based on the signal of the detected particle(s), wherein the device further comprises one or more fluid inlets upstream of the sorting junction and downstream of the detection point for injecting fluid into the sorting channel.

Preferably, this microfluidic device is further characterized by one or more of the following:

(i) the device is designed such that at least the vertical movement of the particle(s) within the microfluidic droplet is constricted in the detection channel at least at the detection point, compared to the same microfluidic droplet when having a spherical shape, (ii) the distance between the sorting junction and the detection point is 500 µm or less (as specified above), preferably less than 10×, 9×, 8×, 7×, 6×, 5× or even 3× of the diameter of the microfluidic droplet in spherical form, and/or (iii) the sorting and/or detection channel of the device is kinked or has a bend as described above.

The device of the eighth aspect can be modified further as described for the device of the fifth aspect of the invention.

A microfluidic device can exist alone or can be a part of a microfluidic system. Thus, in a ninth aspect, the present invention relates to a microfluidics system, comprising:

a microfluidic device according to the fifth, sixth, seventh and/or eighth aspect, and a detection means for detecting at least one particle comprised in a microfluidic droplet in the detection channel at the detection point.

Preferably, the detection means is light sensors, for example photomultiplier tubes, CMOS or CCD cameras, or detection electrodes or an imaging device, preferably real-time, capable of pattern and/or signal recognition, wherein the pattern is for example a microfluidic droplet or a particle within a microfluidic droplet, and wherein the signal is for example a signal from a detectable label as described herein. In a preferred embodiment, the imaging device comprises a camera and a unit for processing image data such as a computer.

In related embodiments, the microfluidics system may further comprise one or more of the following: one or more pumps for introducing fluids into the system and/or through the system; one or more high voltage amplifiers; detection equipment or systems such as a microscope; one or more valves; a laser spectroscopy setup including a laser light source and a light detector; data storage systems; and/or control systems for controlling fluid transport and/or direction within the device, monitoring and controlling environmental conditions to which fluids in the device are subjected, e.g., temperature, current, and the like.

In a preferred embodiment, the microfluidics system comprises a microscope with an objective, wherein the objective has a magnification of at least 20×, preferably of at least 30×, more preferably of at least 40× or even of at least 50×.

In a tenth aspect, the present invention relates to the use of microfluidic droplets, devices and systems of the invention for the methods of invention. In particular, it relates to the use of a microfluidic droplet of the first aspect for the method of the second aspect. Further, it relates to the use of the device of the fifth, sixth, seventh or eighth aspect, or of the microfluidic system of the ninth aspect for the method of the second aspect. Also, it relates to the use of the device of the fifth, sixth, seventh or eighth aspect, or of the microfluidic system of the ninth aspect for the method of the third aspect, in particular wherein the method of the third aspect includes a step (d) of sorting the microfluidic droplet as described above.

The invention is described by way of the following examples which are to be construed as merely illustrative and not limitative of the scope of the invention.

Example 1

In the first example, the present invention is used to select B-cells secreting antibodies binding to a human GPCR. Mice are immunized with the extracellular domain of the GPCR and, subsequent to some booster injections, B-cells are isolated from spleen. These B-cells are then individually encapsulated into droplets, together with anti-murine secondary antibodies labelled with Alexa-Fluor405 (excitation at 405 nm, emission at 450 nm) and 8 µm streptavidin beads coated with both, the biotinlylated extracellular domain of the GPCR and an additional biotinylated dye emitting at a different wavelength than the secondary antibodies (such as bio-Alexa488 or bio-Alexa568). The droplets are incubated for several hours off-chip (to allow for sufficient cellular secretion of primary antibodies inside the droplets) and then re-injected into the above described detection and sorting chip. The fluorescence signal of each droplet is measured by laser spectroscopy for both, the secondary antibody (to quantify binding of the primary antibody to the bead) and the biotinylated dye (to determine how far the bead is outside of the focal plane and/or the maximum intensity of the laser spot). In case a particular encapsulated B-cell secrets antibodies that bind to the GPCR-coated bead, the secondary fluorescently labelled antibodies will also get immobilized on the bead surface. This results in a strong but narrow fluorescence emission peak when the droplet passes the laser. In contrast, if the antibodies secreted by the B-cell do not bind to the bead a broad, low intensity fluorescence peak is observed. In case the bead is inside the focal plane and/or the maximum intensity laser spot, the signal of the biotinylated dye will be maximal. In contrast, if the bead is outside the focal plane and/or the maximum intensity laser spot, the measured fluorescence signal will be weaker. Hence dividing the measured fluorescence peak intensity of the secondary antibodies by the maximum peak intensity of the beads allows to quantitatively determine binding of the primary antibody to the GPCR, independently of the position of the bead inside the droplet. This normalized value can thus be exploited as the sorting criteria for specifically isolating droplets hosting B-cells secreting antibodies binding to the GPCR. After the sorting step, the antibody-encoding genes of individual positively sorted B-cells are amplified by RT-PCR and sequenced to reveal the identity of the desired antibodies.

Example 2

A screen for the agonistic effect of antibodies on GPCRs is carried out. Mice are immunized with the extracellular domain of the GPCR and, subsequent to some booster injections, B-cells are isolated from spleen. In parallel, reporter cells generating a green intracellular fluorescence signal upon GPCR activation (e.g. by expression of short-lived GFP) are stained with Calcein-blue. In a next step, B-cells and reporter cells are co-encapsulated into droplets and incubated for several hours to allow for sufficient secretion of antibodies inside the droplets. Subsequently the droplets are reinjected into a microfluidic device for sorting, for example as described herein. For sorting, the green signal (indicating GPCR activation) is divided by the blue signal (indicating the proximity of the reporter cell to the focal plane and the most intense laser spot) and droplets showing the highest value of this normalized parameter are collected. After the sorting step, the antibody-encoding genes of individual positively sorted B-cells are amplified by RT-PCR and sequenced to reveal the identity of the desired antibodies.

Example 3

A screen for the antagonistic effect of antibodies on GPCRs is carried out. Mice are immunized with the extracellular domain of the GPCR and, subsequent to some booster injections, B-cells are then isolated from spleen. These B-cells are then stained with an unspecific dye such as Calcein-Orange. In parallel, reporter cells generating a green intracellular fluorescence signal upon GPCR activation are stained with Calcein-blue. In a next step, B-cells, reporter cells and a drug activating the GPCR of interest are co-encapsulated into droplets and incubated for several hours to allow for sufficient secretion of antibodies inside the droplets. In all droplets that do not contain any B-cell secreting antagonistic antibodies, the reporter cell will show a strong green signal (due to the presence of the drug). In contrast, droplets hosting B-cells secreting antagonistic antibodies will eliminate this reporter signal and indicate the phenotype of interest. However, if a particular droplet simply does not host a reporter cell, the same phenotype (in the green channel) will be detected. Without additional measures this would inevitably lead to the selection of many false positive B-cells. To overcome this problem, the droplets are analyzed in a multicolour fashion after being reinjected into a sorting device with several special features to increase the sensitivity: Using a chip with a detection channel in which the droplets are compressed at least in the z-dimension and using a sorting channel in a 45° angle the droplets are first analyzed for the presence of exactly one B-cell (one orange peak) and one reporter cell (one blue peak). Only droplets fulfilling this criteria and additionally showing no or at least a strongly reduced assay signal in the green channel are sorted. After the sorting step, the antibody-encoding genes of individual positively sorted B-cells are amplified by RT-PCR and sequenced to reveal the identity of the desired antibodies.

Example 4

A screen for the specific binding of antibodies to an antigen such as matrix metalloproteinase-1 (MMP-1) is carried out. This screen includes a direct counter-screen against antibodies that also bind to MMP-2. Mice are immunized with a peptide of MMP-1 and, subsequent to some booster injections, B-cells are isolated from spleen. These B-cells are then individually encapsulated into droplets, together with anti-murine secondary antibodies labelled with Alexa-Fluor405 (excitation at 405 nm, emission at 450 nm) and 8 μm streptavidin beads coated with both, the biotinlylated peptide of MMP-1 and bio-488. Furthermore, 8 μm streptavidin coated beads coated with MMP-2 and bio-Alexa568 are additionally co-encapsulated into the droplets. For sorting, only droplets showing a strong value for the fluorescence signal at 405 nm divided by the signal intensity at 488 (normalized value indicating efficient binding to the target antigen MMP-1) and, at the same time, showing no or only a weak value for the fluorescence signal at 405 nm divided by the signal intensity at 568 (normalized value indicating undesired binding to MMP-2) are collected. This way, highly specific binders of MMP-1 that do not bind to MMP-2 can be identified. After the sorting step, the antibody-encoding genes of individual positively sorted B-cells are amplified by RT-PCR and sequenced to reveal the identity of the desired antibodies.

Example 5

The reliable detection of stained cells inside a microfluidic droplet is challenging, as the cells can float into an out of the focal plane and/or the centre of the laser spot, resulting in highly variable intensities of the emitted light. To overcome this, the inventors have designed a novel sorting chip with a special geometry (FIGS. 3 and 4): First of all, the part of the channel in which the detection occurs (onto which the laser beam is focused) is narrower and shallower compared to the rest of the chip (e.g. <50% compared to the remaining channels). This means the droplets are converted to plugs (droplets that completely fill the channel) and the encapsulated cells have less spatial freedom in both, the y-dimension (in which the cell can be closer or further apart from the centre of the laser spot) and the z-dimension (in which the cell can be closer or further apart from the focal plane). Noteworthy, designing the entire chip as a narrow and shallow channel is not feasible, as otherwise clogging occurs much more frequently. In contrast, the sorting chip of the invention has different depths and widths for the analysis and the sorting step.

Sensitivity of the fluorescence readout can also be increased by using high magnification objectives. However, for sorting devices able to handle droplets large enough for the cultivation of mammalian cells (typically ~100 μm in diameter) it is very difficult to have the analysis point and the sorting divider in the same field of view when using for example a 40× objective. This is due to the fact that large droplets demand larger channel dimensions as compared to 30 μm droplet sorters, but also because of the significant space requirements of the electrodes used for dielectrophoretic sorting. The inventors have managed to design a very compact sorting chip in which the analysis point and the sorting divider are in the same field of view (with a distance between the two of less than 500 μm), even when using a 40× objective. The compact design is also achieved by having a 45° angled kink in the channel in which the droplets are detected and sorted (see FIG. 4). A further feature of this sorting chip are additional oil inlets downstream of the constriction, but upstream of the sorting divider. This allows to fine tune the trajectory of the droplets towards the sorting junction. A chip is already advantageous if comprising one of these novel features, but particularly advantageous if more than one or all of them are combined.

Example 6

6 μm Fluoresbrite beads (beads emitting simultaneously at different wavelength; commercially available from Polysciences Inc.) were encapsulated into droplets and analyzed for the resulting fluorescence signals. All beads have approximately the same number of fluorophores and should hence show very little variation in terms of the fluorescence intensity. However, when only analyzing a single fluorescence channel (e.g. green or blue range), a very wide distribution of fluorescence intensities is observed (see FIG. 7 A, B). This is due to the fact that the beads are freely floating inside the droplets, meaning that they can be inside or outside the focal plane and/or the center of the laser spot. However, when normalizing the green signal to the blue signal (e.g. by dividing the corresponding values) this effect can be minimized (see FIG. 7 C). All events are roughly on the same diagonal line, meaning that sorting of these events according to a normalized dual-colour readout results in the collection of beads having comparable fluorescence intensities, despite their strong signal variation when only looking at a single fluorescence channel.

The invention claimed is:

1. A microfluidic droplet comprising a first particle associated with an amount of a first detectable label, and a potential particle binding partner associated with an amount of a second detectable label, wherein the amount of the first detectable label is known and/or substantially identical to the amount of the first detectable label associated with a further particle comprised in a further microfluidic droplet, wherein the first detectable label is different from the second detectable label, and wherein the further microfluidic droplet is comprised in a plurality of microfluidic droplets also comprising said microfluidic droplet comprising said first particle, and wherein the potential particle binding partner is one of an antibody, antibody derivative, antibody mimetic, a bacteriophage, an mRNA-polypeptide complex, an mRNA-ribosome-polypeptide complex, a cell, a virus, a peptide, a protein, a nucleic acid, an aptamer and a small molecule.

2. The microfluidic droplet of claim 1, wherein the first particle is associated with the second detectable label via binding to the potential particle binding partner.

3. The microfluidic droplet of claim 1, wherein the first and further particle are selected from the group consisting of a cell, a virus, a bead, a protein and a nanoparticle.

4. The microfluidic droplet of claim 1, wherein the microfluidic droplet further comprises, associated with an amount of a third detectable label, (i) a particle non-binder or (ii) a second particle not binding the potential particle binding partner.

5. A method for quantifying the binding between a particle and a potential particle binding partner in a microfluidic droplet according to claim 1, comprising the steps of
(i) measuring the signal of the first detectable label,
(ii) measuring the signal of the second detectable label, and
(iii) normalizing the signal of the second detectable label using the signal of the first detectable label,
wherein the normalized signal of the second detectable label represents the quantity of binding between the particle and the potential particle binding partner.

6. A method for screening potential particle binding partners, comprising the steps of:
(a) feeding a microfluidic droplet comprising a potential particle binding partner-producing cell and a reporter cell into a detection channel, the detection channel comprising a detection point, and wherein the reporter cell signals the effect of a potential particle binding partner produced by the potential particle binding partner-producing cell via a second detectable label, and wherein the reporter cell further comprises a first detectable label, and
(b) detecting a first detectable label and the second detectable label of the reporter cell, comprised in the microfluidic droplet at the detection point, and
(c) normalizing the signal of the second detectable label using the signal of the first detectable label,
wherein the potential particle binding partner is one of an antibody, antibody derivative, antibody mimetic, a bacteriophage, an mRNA-polypeptide complex, an mRNA-ribosome-polypeptide complex, a cell, a virus, a peptide, a protein, a nucleic acid, an aptamer and a small molecule.

7. The method according to claim 6, further comprising constricting at least the vertical movement of said cells within the microfluidic droplet at least at the detection point in the detection channel, compared to the same microfluidic droplet when having a spherical shape.

8. The method according to claim 6, further comprising step (d) sorting the microfluidic droplet according to the normalized signal.

9. The method according to claim 6, further comprising a preparation step (a') before step (a), comprising the encapsulation of the potential particle binding partner-producing cell and reporter cell into the microfluidic droplet and incubating the potential particle binding partner-producing cell and the reporter cell for an amount of time sufficient for secretion of antibodies inside the droplets.

10. A method for quantifying the effect of a potential particle binding partner on a particle in a microfluidic droplet according to claim 1, comprising the steps of
   (i) measuring the signal of the first detectable label,
   (ii) measuring the signal of the second detectable label, and
   (iii) normalizing the signal of the second detectable label using the signal of the first detectable label,
   wherein the normalized signal of the second detectable label represents the quantity of effect of the potential particle binding partner on the particle.

11. The method according to claim 10, wherein the particle is a reporter cell, and wherein the reporter cell signals by the second detectable label the effect of the particle binding partner on the reporter cell.

\* \* \* \* \*